United States Patent [19]

Erdelmeier et al.

[11] Patent Number: 6,093,532
[45] Date of Patent: Jul. 25, 2000

[54] METHOD FOR STORING A BIOLOGICAL ORGAN TRANSPLANT GRAFT USING A BENZISOSELEN-AZOLINE OR -AZINE COMPOUND

[75] Inventors: Irène Erdelmeier, Paris; Jean Chaudiere, St. Maur des Fosses; Marc Moutet, Bagneux; Jean-Claude Yadan, Paris, all of France

[73] Assignee: Oxis Isle of Man, Limited, Portland, Oreg.

[21] Appl. No.: 09/303,421

[22] Filed: May 3, 1999

Related U.S. Application Data

[62] Division of application No. 08/549,809, filed as application No. PCT/FR95/00447, Apr. 7, 1995, Pat. No. 5,968,920.

[30] Foreign Application Priority Data

Jul. 4, 1994 [FR] France ................ 94 04107

[51] Int. Cl.[7] .............. C12N 5/00; C12N 5/02; G01N 31/00
[52] U.S. Cl. .............. 435/1.1; 435/1.2; 435/1.3; 435/325; 435/366; 436/18
[58] Field of Search ............... 435/1.1, 1.2, 1.3, 435/325, 326; 436/18

[56] References Cited

PUBLICATIONS

Yoshikawa et al., Cancer Research 33, 1617–1620, Apr. 1995.
Trush et al., Free Radical Biology & Medicine, vol. 10, pp 201–209, 1991.

*Primary Examiner*—Mukund J. Shah
*Assistant Examiner*—Bruck Kifle
*Attorney, Agent, or Firm*—Dennison, Scheiner, Schultz & Wakeman

[57] ABSTRACT

The invention concerns novel benzisoselen-azoline and -azine derivatives. These novel derivatives have the following general formula (II):

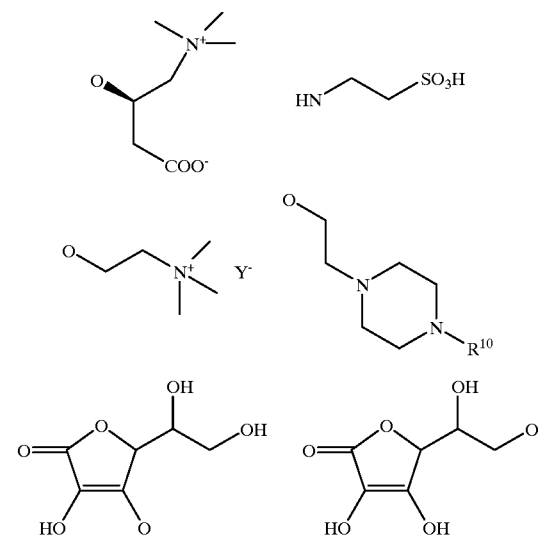

General formula II where:
$R^1$ to $R^8$ and $R^{10}$ have various meanings, in particular H, alkyl, etc . . . ;

$R^9 =$ $Y^-$ represents the anion of a pharmaceutically acceptable anion; n=0, 1; m=0, 1, 2; p=1, 2, 3; q=2, 3, 4; r=0, 1; and their pharmaceutically acceptable salts of acids or bases; there being no more than one substituent $R^9$ in each molecule with general formula II. These novel derivatives can be used in medication.

12 Claims, 5 Drawing Sheets

METHOD FOR STORING A BIOLOGICAL ORGAN TRANSPLANT GRAFT USING A BENZISOSELEN-AZOLINE OR -AZINE COMPOUND

This is a divisional of application Ser. No. 08/549,809, filed Jan. 30, 1996 now U.S. Pat. No. 5,968,920 which is a national stage entry of PCT/FR95/00447 filed Apr. 7, 1995.

The present invention concerns the use of novel compounds with a benzisoselenazoline structure gem-disubstituted in the 3 position and benzisoselenazine compounds gem-disubstituted in the 4 position, as antioxidants, a method for their preparation and pharmaceutical compositions containing these compounds.

PRIOR ART

The majority of mammalian tissues and cells possess enzymes termed glutathione peroxidases which allow endogenous or exogenous cytotoxic hydroperoxides to degrade.

These antioxidizing and cytoprotective enzymes play a central role in preventing "oxidizing stress" and its deleterious consequences.

They catalyse the reduction of hydrogen peroxide (reaction 1) or organic hydroperoxides (reaction 2) by reduced glutathione (GSH):

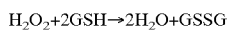  reaction 1

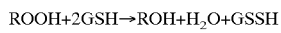  reaction 2

Glutathione peroxidases are selenium enzymes. Three sub-families have been described:

intra-cellular enzymes, which are hydrosoluble and have a symmetrical tetrameric structure (see L. Flohé, "Structures and Catalytic Mechanism of Glutathione Peroxidase", in Glutathione Centennial, (1989); N. Taniguchi, T. Higashi, Y. Sakamoto and A. Meister, Eds: Academic Press, pp 103–114);

intra-cellular enzymes which are partially bound to membranes and have a monomeric structure (see F. Ursini et al., Biochem. Biophys. Acta, (1982), 710, pp 197–211);

and finally, glutathione peroxidase which is specific to blood plasma, a tetrameric enzyme whose N-terminal end is specifically glycosylated (see K. Takahashi et al., J.Biochem, (1990), 108, pp 145–148).

The active sites of these enzymes all possess an essential selenium atom in the form of a selenocysteine residue incorporated into the polypeptide chain.

The essential character of the selenium in the active site is well documented (see J. W. Forstrom et al., Biochemistry (1978), 17, 2639–2644 and A. Wendel et al., Hoppe-Seyler's Z.Physiol.Chem., (1978), 359, pp 1035–1036).

In cases of nutritional deficiency of selenium, the concentrations and activities of the glutathione peroxidases gradually fall (see Y. X. Wang and J. Kiem, Biological Trace Elements Res., (1988), 15, p 89).

Further, controlled mutagenesis experiments have shown that replacement of a selenium atom in the active site by a sulfur atom results in a large fall in catalytic activity (see C. Rocher et al., Eur. J. Biochem., (1992), 205, pp 955–960).

In the human and animal, selenite and selenate salts and L-selenomethionine constitute three natural forms of selenium supply.

The nutritional supply of selenium is a limiting factor in the biosynthesis of glutathione peroxidases, but an increase in the glutathione peroxidase activity with such a supply of selenium follows a rapid saturation curve. Beyond the saturation plateau, an increase in the nutritional supply of selenium results in marked toxicity (see O. A. Levander, Ann. Rev. Nutr., (1987), 7, pp 227–250). The interval between the quantities of selenium required from natural origins and their toxicity limit is thus small.

Experiments involving intra-cellular microinjection of erythrocytic enzyme have shown its very marked protective effect on the viability of fibroblasts or endothelial cells exposed to an oxidizing stress (see C. Michiels et al., Experiment. Cell Res., (1988), 179, pp 581–589).

The use of a glutathione peroxidase of natural origin for therapeutic use is, however, difficult to envisage for the following reasons:

the purified enzymes have insufficient stability;

there is no effective method for ensuring intra-cellular targeting;

they cannot be administered orally.

To eliminate these difficulties, a certain number of low molecular weight organoselenium compounds have been synthesized.

The biochemical and pharmacological properties of organoselenium compounds which have been synthesized and studied have recently been reviewed (see M. J. Parnham and E. Graf, Progress in Drug Res., (1991), 36, pp 9–47).

Organoselenium compounds with glutathione peroxidase activity generally produce selenol and/or diselenide type catalytic intermediates.

Of those compounds, 2-phenyl-3-one-benzisoselenazoline(2H) and some of its derivatives do not appear to have a major toxic effect (See A. Wendel et al., Biochem. Pharmacol., (1984), 33, pp 3241–3245 and S. D. Mercurio and G. F. Combs, Biochem. Pharmacol, (1986), 35, pp 4505–4509).

In the presence of excess glutathione GSH, however, 2-phenyl-3-one-benzisoselenazoline(2H) produces a derivative which is only very slightly soluble in water, which limits its pharmacological applications.

The toxicity of selenol and/or diselenide type organoselenium compounds is largely due to catalytic reduction of oxygen to a superoxide and hydrogen peroxide (see J. Chaudiére et al., Arch. Biochem. Biophys., (1992), 296, pp 328–336).

One aim of the present invention is to provide organoselenium compounds with a glutathione peroxidase type catalytic activity in the presence of physiological concentrations of glutathione GSH.

These compounds must be capable of penetrating into target tissues and cells, they must be soluble in water at active concentrations and they must not efficiently reduce oxygen to toxic by-products.

These aims are achieved by the invention which is based on the provision of novel benzisoselen-azoline and -azine derivatives whose antioxidant and cytoprotective activities are described, also a method for their preparation.

From a chemical viewpoint, some benzisoselenazolone derivatives have been described in the literature. In general, most of these derivatives have been produced by reacting a lithiated aromatic derivative, generated either by halogen-metal exchange or by deprotonation with a strong base, with metallic selenium (Se°) (see C. Lambert et al., Synthetic Comm., (1991), 21, pp 85–98).

One of the described aims of this invention is to provide a novel method of introducing selenium into a halogenated benzene nucleus, substituted in the 2 position, by reaction with a nucleophilic selenium derivative such as a selenocyanate salt, for example potassium selenocyanate, which may be generated in situ, in the presence of a cuprous ($Cu^I$) salt.

DESCRIPTION OF THE INVENTION

The aim of the present invention is:

1) to solve the novel technical problem consisting of providing novel benzisoselen-azoline and -azine derivatives having good antioxidizing and cytoprotective activity, which can thus constitute a valuable active ingredient in pharmaceutical compositions;
2) to solve the novel technical problem described above with a solution which provides a method for the preparation of these compounds which is easy to carry out.

These aspects of the technical problem described above are simultaneously solved by the present invention by a simple solution, with a preparation method which is relatively easy to carry out and which provides good yields.

In a first aspect, the present invention provides novel benzisoselen-azoline and -azine derivatives with the following general formula (II):

General formula II

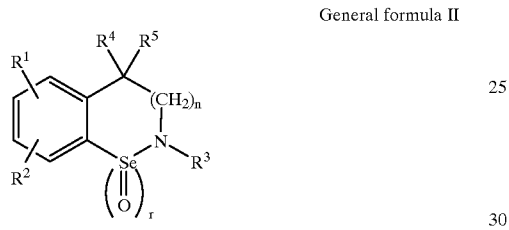

where:
  $R^1$=hydrogen; lower alkyl; —$OR^6$; —$(CH_2)_mNR^6R^7$; —$(CH_2)_qNH_2$; —$(CH_2)_mNHSO_2(CH_2)_2NH_2$; —$NO_2$; —CN; —$SO_3H$; —$N^+(R^5)_2O^-$; F; Cl; Br; I; —$(CH_2)_mR^8$; —$(CH_2)_mCOR^8$; —$S(O)NR^6R^7$; —$SO_2NR^6R^7$; —$CO(CH_2)_pCOR^8$; $R^9$;
  $R^2$=hydrogen; lower alkyl; —$OR^6$; —$(CH_2)_mNR^6R^7$; —$(CH_2)_qNH_2$; —$(CH_2)_mNHSO_2(CH_2)_2NH_2$; —$NO_2$; —CN; —$SO_3H$; —$N^+(R^5)_2O^-$; F; Cl; Br; I; —$(CH_2)_mR^8$; —$(CH_2)_mCOR^8$; —$S(O)NR^6R^7$; —$SO_2NR^6R^7$; —$CO(CH_2)_pCOR^8$; $R^9$;
  $R^3$=hydrogen; lower alkyl; aralkyl; substituted aralkyl; —$(CH_2)_mCOR^8$; —$(CH_2)_qR^8$; —$CO(CH_2)_pCOR^8$; —$(CH_2)_mSO_2R^8$; —$(CH_2)_mS(O)R^8$;
  $R^4$=lower alkyl; aralkyl; substituted aralkyl; —$(CH_2)_pCOR^8$; —$(CH_2)_pR^8$; F;
  $R^5$=lower alkyl; aralkyl; substituted aralkyl;
  $R^6$=lower alkyl, aralkyl; substituted aralkyl; —$(CH_2)_mCOR^8$; —$(CH_2)_qR^8$;
  $R^7$=lower alkyl; aralkyl; substituted aralkyl; —$(CH_2)_mCOR^8$;
  $R^8$=lower alkyl; aralkyl; substituted aralkyl; aryl; substituted aryl; heteroaryl; substituted heteroaryl; hydroxy; lower alkoxy; $R^9$;

$R^9$ =

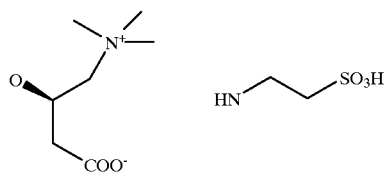

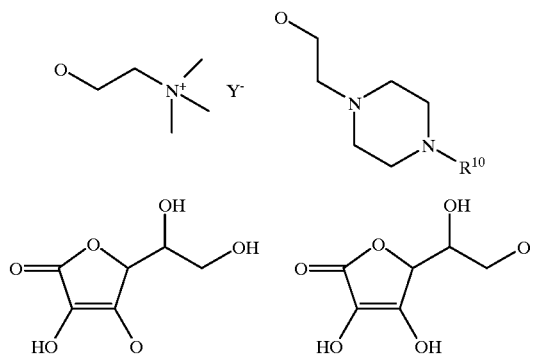

$R^{10}$=hydrogen; lower alkyl; aralkyl or substituted aralkyl; aryl or substituted aryl;
  $Y^-$ represents the anion of a pharmaceutically acceptable acid;
  n=0, 1;
  m=0, 1, 2;
  p=1, 2, 3;
  q=2, 3, 4;
  r=0, 1;
  and their pharmaceutically acceptable salts of acids or bases;
  there being no more than one substituent $R^9$ in each molecule with general formula II.

In the description and claims:
  the term lower alkyl or alkoxy means linear or branched groups containing 1 to 6 carbon atoms;
  the term heteroalkyl means any mono-or bicyclic aromatic nucleus, each ring containing 5 to 6 vertices and including one or possibly more identical or different heteroatoms in its carbon backbone, selected from nitrogen, oxygen and sulfur, and which may be substituted;
  the term substituted as applied to aryl, aralkyl or heteroalkyl groups means that these are substituted in the aromatic portion by one or more identical or different groups selected from lower alkyl, trifluoromethyl, lower alkoxy, hydroxy, nitro, amino, alkylamino; dialkylamino; sulfonyl; sulfonamide; sulfoalkyl; carboxy; carbalkoxy or one or more hydrogen atoms;
  when $R^1$ represents —COOH or —$SO_3H$, the invention also includes addition salts with a pharmaceutically acceptable base;
  when $R^1$ represents —$NR^6R^7$, the invention also includes addition salts with a pharmaceutically acceptable acid;
  when $R^8$ represents OH, the invention also includes addition salts to a pharmaceutically acceptable base.

Non limiting examples of pharmaceutically acceptable acids are hydrochloric, hydrobromic, hydriodic, sulfuric, tartaric, methanesulfonic, trifluoromethanesulfonic acid, etc. . .

Non limiting examples of pharmaceutically acceptable bases are sodium and potassium hydroxides, alkali or alkaline-earth metal carbonates or organic bases such as triethylamine or arginine, etc. . .

In a second aspect, the present invention concerns the use of benzisoselen-azoline and -azine compounds with the following general formula (I):

General formula I

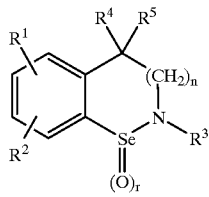

where:
R¹=hydrogen; lower alkyl; —OR⁶; —(CH₂)ₘNR⁶R⁷; —(CH₂)qNH₂; —(CH₂)ₘNHSO₂(CH₂)₂NH₂; —CN; —SO₃H; F; Cl; Br; I; —(CH₂)ₘR⁸; —(CH₂)ₘCOR⁸; —S(O)NR⁶R⁷; —SO₂NR⁶R⁷; —CO(CH₂)pCOR⁸; R⁹;

R²=hydrogen; lower alkyl; —OR⁶; —(CH₂)ₘNR⁶R⁷; —(CH₂)qNH₂; —(CH₂)ₘNHSO₂(CH₂)₂NH₂; —CN; —SO₃H; F; Cl; Br; I; —(CH₂)ₘR⁸; —(CH₂)ₘCOR⁸; —S(O)NR⁶R⁷; —SO₂NR⁶R⁷; —CO(CH₂)pCOR⁸; R⁹;

R³=hydrogen; lower alkyl; aralkyl; substituted aralkyl; —(CH₂)ₘCOR⁸; —(CH₂)qR⁸; —CO(CH₂)pCOR⁸; —(CH₂)ₘSO₂R⁸; —(CH₂)ₘS(O)R⁸;

R⁴=lower alkyl; aralkyl; substituted aralkyl; —(CH₂)pCOR⁸; —(CH₂)pR⁸; F;

R⁵=lower alkyl; aralkyl; substituted aralkyl;

R⁶=lower alkyl; aralkyl; substituted aralkyl; —(CH₂)ₘCOR⁸; —(CH₂)qR⁸;

R⁷=lower alkyl; aralkyl; substituted aralkyl; —(CH₂)ₘCOR⁸;

R⁸=lower alkyl-aralkyl; substituted aralkyl; aryl; substituted aryl; heteroaryl; substituted heteroaryl; hydroxy; lower alkoxy; R⁹;

R⁹ =

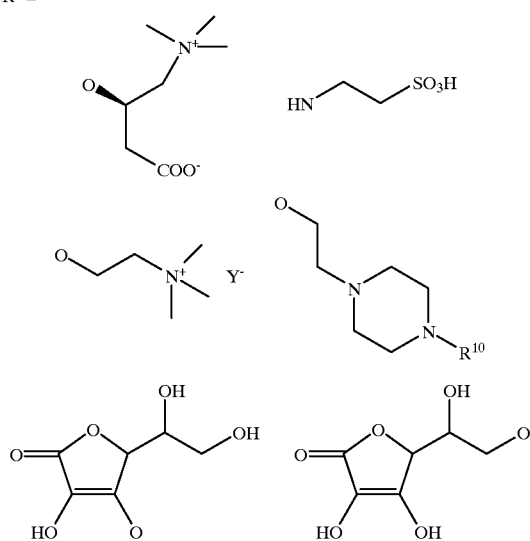

R¹⁰=hydrogen; lower alkyl, aralkyl or substituted aralkyl; aryl or substituted aryl;
Y⁻ represents the anion of a pharmaceutically acceptable acid;
n=0, 1;
m=0, 1, 2;
p 1, 2, 3;
q=2, 3, 4;
r=0, 1;

and their pharmaceutically acceptable salts of acids or bases;
there being no more than one substituent R⁹ in each molecule with general formula I,
as antioxidizing agents.

The invention also includes therapeutic treatment methods corresponding to this use, as would be understood by the skilled person.

In an advantageous embodiment, the present invention concerns the use of compounds with general formula I described above for the manufacture of a pharmaceutical composition with antioxidizing activity, in particular for:

treating pathologies in which an overproduction of cytotoxic hydroperoxides contributes to functional alterations in cells or tissues;

treating pathologies with an inflammatory and/or ischemic component:
vascular: such as treatment to prevent arterial re-stenosis following angioplastic intervention, treatment to prevent arterial stenosis following arterial allografts, treatment of intermittent claudication in patients with obstructive ischemia of the lower limbs; treatment of cerebro-vascular injuries of ischemic origin; preventative or curative treatment of adult (ARDS) or infant (IRDS) respiratory distress syndrome;
articulatory: such as the treatment of rheumatoid arthritis;

treating ophthalmic pathologies: such as treating acute ophthalmic allergies, treating retinal changes associated with a macular degeneration; treating glaucoma;

treating immune system dysfunctions such as treating acquired immunodeficiency syndrome (AIDS);

protective treatment against intoxication by xenobiotic substances generating free radicals, in particular during cancer chemotherapy;

storing organs for transplanting such as the heart, liver, kidney and lung; by adding one of the compounds of the present invention to storage media for these organs.

In these examples, the active ingredient can be administered orally, rectally or topically (for example as a salve for ophthalmic applications), or by intramuscular or intravenous injection.

In a third advantageous embodiment, the benzisoselenazoline or -azine with general formula (I) above is present in a quantity in the range 0.1% to 5% by weight with respect to the total final composition weight, preferably in the range 0.1% to 1% by weight.

In a further advantageous embodiment, the present invention concerns the use of the composition in the form of a unit dose which may comprise 1 milligram (mg) to 500 mg of the benzisoselena-zoline or -azine derivative with general formula (I), optionally in a pharmaceutically acceptable excipient, vehicle or support.

In a third aspect, the present invention provides a pharmaceutical composition, in particular with antioxidizing activity, characterized in that it comprises, as an active ingredient, at least one benzisoselenazoline or -azine compound with the following general formula (I):

General formula I

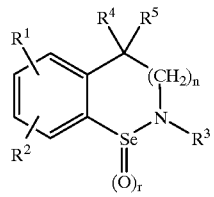

where:
R¹=hydrogen; lower alkyl; —OR⁶; —(CH₂)ₘNR⁶R⁷; —(CH₂)qNH₂; —(CH₂)ₘNHSO₂(CH₂)₂NH₂; —CN; —SO₃H; F; Cl; Br; I; —(CH₂)ₘR⁸; —(CH₂)ₘCOR⁶; —S(O)NR⁶R⁷; —SO₂NR⁶R⁷; —CO(CH₂)pCOR⁸; R⁹;

R²=hydrogen; lower alkyl; —OR⁶; —(CH₂)ₘNR⁶R⁷; —(CH₂)qNH₂; —(CH₂)ₘNHSO²(CH₂)₂NH₂; —CN; —SO₃H; F; Cl; Br; I; —(CH₂)ₘR⁸; —(CH₂)ₘCOR⁸; —S(O)NR⁶R⁷; —SO₂NR⁶R⁷; —CO(CH₂)pCOR⁸; R⁹;

R³=hydrogen; lower alkyl; aralkyl; substituted aralkyl; —(CH₂)ₘCOR⁸; —(CH₂)qR⁸; —CO(CH₂)pCOR⁸; —(CH₂)ₘSO₂R⁸; —(CH₂)ₘS(O)R⁸;

R⁴=lower alkyl; aralkyl; substituted aralkyl; —(CH₂)pCOR⁸; —(CH₂)pR⁸; F;

R⁵=lower alkyl; aralkyl; substituted aralkyl;

R⁶=lower alkyl; aralkyl; substituted aralkyl; —(CH₂)ₘCOR⁸; —(CH₂)qR⁸;

R⁷=lower alkyl; aralkyl; substituted aralkyl; —(CH₂)ₘCOR⁸;

R⁸=lower alkyl; aralkyl; substituted aralkyl; aryl; substituted aryl; heteroaryl; substituted heteroaryl; hydroxy; lower alkoxy; R⁹;

R⁹ =

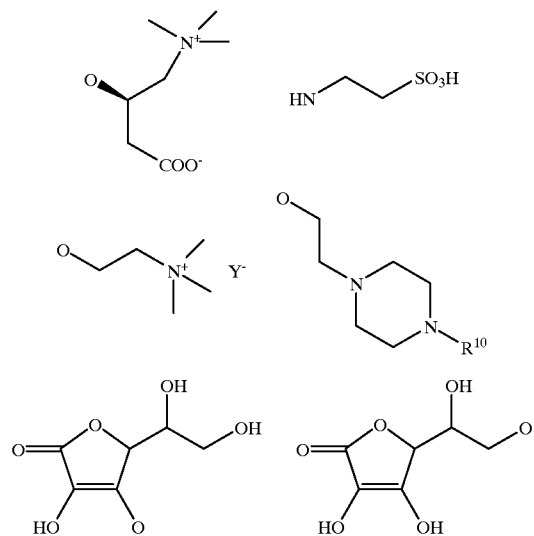

R¹⁰=hydrogen; lower alkyl; aralkyl or substituted aralkyl; aryl or substituted aryl;
Y⁻ represents the anion of a pharmaceutically acceptable acid;
n=0, 1;
m=0, 1, 2;
p=1, 2, 3;
q=2, 3, 4;
r 0, 1;

and their pharmaceutically acceptable salts of acids or bases;
there being no more than one substituent R⁹ in each molecule with general formula I,
optionally in a pharmaceutically acceptable excipient, support or vehicle.

Other particular embodiments of this composition will become clear from the preceding description and will also be clear to the skilled person from the following description, including the examples.

As stated above, the benzisoselen-azoline or -azine compounds with formula (I) defined above constitute valuable antioxidizing agents. As such, they constitute valuable active ingredients for therapeutic use.

Potential therapeutic applications of compounds with general structure (I) generally include the treatment of any physiopathological condition in which an overproduction of cytotoxic hydroperoxides contributes to functional changes in cells or tissues. Such overproduction of hydroperoxides may be the consequence of the activation of metabolic routes such as flavine or cytochrome P-450 oxygenases, or monoamine oxidases. It may also be due to the activation of endothelial cells (xanthine oxidase, 15-lipoxygenase), blood platelets (cyclooxygenase and 12-lipoxygenase) and inflammatory cells (NADPH oxidase and 5-lipoxygenase) such as neutrophiles, macrophages or lymphocytes. It can also be due to intoxication by a xenobiotic substance such as anthracyclines, nitro-imidazoles or dipyridinium type derivatives which generate free radicals.

They particularly include:
treating pathologies with an inflammatory and/or ischemic component;
vascular: such as treatment to prevent arterial re-stenosis following angioplastic intervention, treatment to prevent arterial stenosis following arterial allografts, treatment of intermittent claudication in patients with obstructive ischemia of the lower limbs; treatment of cerebro-vascular injuries of ischemic origin; preventative or curative treatment of adult (ARDS) or infant (IRDS) respiratory distress syndrome;
articulatory: such as the treatment of rheumatoid arthritis;
treating ophthalmic pathologies: such as treating acute ophthalmic allergies, treating retinal changes associated with macular degeneration; treating glaucoma;
treating immune system dysfunctions such as treating acquired immunodeficiency syndrome (AIDS);
protective treatment against intoxication by xenobiotic substances generating free radicals, in particular during cancer chemotherapy;
storing organs for transplanting such as the heart, liver, kidney and lung; by adding one of the compounds of the present invention to storage media for these organs.

In a further advantageous embodiment, the benzisoselen-azoline or -azine derivative with general formula (I) above is present in a quantity in the range 0.1% to 5% by weight with respect to the total final composition weight, preferably in the range 0.1% to 1% by weight.

For therapeutic applications, the derivatives with general formula (I) above are advantageously packaged in the form of a unit dose which may comprise 1 mg to 500 mg of the benzisoselenazoline or-azine derivative with general formula (I), optionally in a pharmaceutically acceptable excipient, vehicle or support.

Such pharmaceutically acceptable excipients, vehicles or supports are well known to the skilled person and are not detailed here.

In these examples, the active ingredient can be administered orally, rectally or topically (for example, as a salve for ophthalmic application), or by intramuscular or intravenous injection.

The antioxidizing and therapeutic or pharmacological activities of derivatives with general formula (I) above have been demonstrated by reliable tests comprising:

a) measuring glutathione peroxidase activity;

b) measuring the reducing activity by monoelectron transfer;

c) measuring the cytoprotective effect in human endothelial cells such as those of the umbilical vein (HUVEC) used between the first and second passage, or from a HUVEC clone immortalised by viral transfection.

Because of these antioxidizing and therapeutic or pharmacological activities, the benzisoselen-azoline or -azine derivatives with general formula (I) above can be used in the therapeutic applications described above, in particular:

the treatment of pathologies in which an overproduction of cytotoxic hydroperoxides contributes to functional changes in the cells or tissues;

the treatment of pathologies with an inflammatory and/or ischemic vascular component such as treatment to prevent re-stenosis following angioplastic intervention, treatment to prevent arterial stenosis following arterial allografts, treatment of intermittent claudication in patients with obstructive ischemia of the lower limbs; treatment of cerebro-vascular injuries of ischemic origin; treating glaucoma.

In a fourth aspect, the present invention provides a method for the production of compounds with the following general formula (II):

General formula II

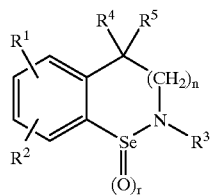

where:

$R^1$=hydrogen; lower alkyl; —$OR^6$; —$(CH_2)_m NR^6 R^7$; —$(CH_2)_q NH_2$; —$(CH_2)_m NHSO_2(CH_2)_2 NH_2$; —$NO_2$; —CN; —$SO_3H$; —$N^+(R^5)_2 O^-$; F; Cl; Br; I; —$(CH_2)_m R^8$; —$(CH_2)_m COR^8$; —$S(O)NR^6 R^7$; —$SO_2 NR^6 R^7$; —$CO(CH_2)_m COR^8$; $R^9$;

$R^2$=hydrogen; lower alkyl; —$OR^6$; —$(CH_2)_m NR^6 R^7$; $(CH_2)_q NH_2$; —$(CH_2)_m NHSO_2(CH_2)_2 NH_2$; —$NO_2$; —CN; —$SO_3H$; —$N^+(R^5)_2 O^-$; F; Cl; Br; I; —$(CH_2)_m R^8$; —$(CH_2)_m COR^8$; —$S(O)NR^6 R^7$; —$SO_2 NR^6 R^7$; —$CO(CH_2)_p COR^8$; $R^9$;

$R^3$=hydrogen; lower alkyl; aralkyl; substituted aralkyl; —$(CH_2)_m COR^8$; —$(CH_2)_q R^8$; —$CO(CH_2)_p COR^8$; —$(CH_2)_m SO_2 R^8$; —$(CH_2)_m S(O)R^8$;

$R^4$=lower alkyl; aralkyl; substituted aralkyl; —$(CH_2)_p COR^8$; —$(CH_2)_p R^8$; F;

$R_5$=lower alkyl, aralkyl; substituted aralkyl;

$R^6$=lower alkyl; aralkyl; substituted aralkyl; —$(CH_2)_m COR^8$; —$(CH_2)_q R^8$;

$R^7$=lower alkyl; aralkyl; substituted aralkyl; —$(CH_2)_m COR^8$;

$R^8$=lower alkyl; aralkyl; substituted aralkyl; aryl; substituted aryl; heteroaryl; substituted heteroaryl; hydroxy; lower alkoxy; $R^9$;

$R^9$ =

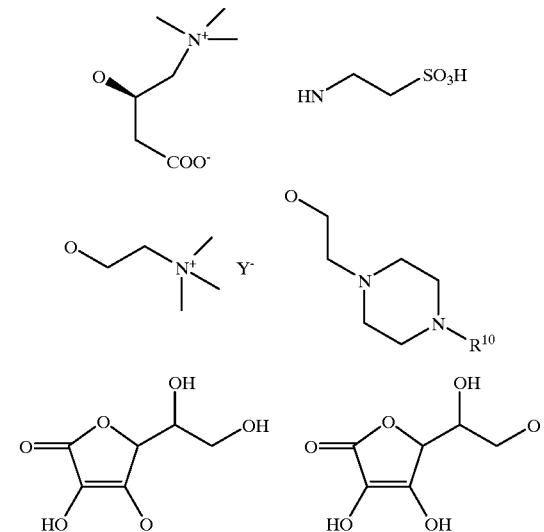

$R^{10}$=hydrogen; lower alkyl; aralkyl or substituted aralkyl; aryl or substituted aryl;

$Y^-$ represents the anion of a pharmaceutically acceptable acid;

n=0, 1;

m=0, 1, 2;

p=1, 2, 3;

q=2, 3, 4;

r=0, 1;

and their pharmaceutically acceptable salts of acids or bases;

there being no more than one substituent $R^9$ in each molecule with general formula II;

characterized in that it comprises the following essential steps (see Scheme 1):

a) preparing or using an orthohalogenophenyl-acetonitrile derivative gem-disubstituted in the 2 position, then depending on the series considered: either b1) hydrolysing the nitrile derivative to an amide derivative, c1) transforming the amide derivative to an amine derivative by a transposition reaction using normal methods, d1) reacting the amine compound with a nucleophilic selenium compound which may be generated in situ, in the presence of a copper salt, in a polar organic solvent, to produce the corresponding benzisoselenazoline derivative, e1) N-alkylating or N-acylating the latter using normal procedures, f1) finally, oxidizing the derivative obtained at the selenium atom if necessary, using normal procedures; or b2) reducing the nitrile derivative to an amine derivative using, for example, borane in an ethereal solvent such as tetrahydrofuran, c2) reacting the amine compound with a nucleophilic selenium derivative, which may be generated in situ, in the presence of a copper salt, in a polar organic solvent, to produce the corresponding benzisoselenazine derivative, d2) N-alkylating or N-acylating the latter using normal procedures, e2) finally, oxidizing the derivative obtained at the selenium atom if necessary, using normal procedures.

A further implementation of the method is characterized in that the nucleophilic selenium compound is preferably a selenocyanate salt such as potassium selenocyanate which can be:

either generated in situ from selenium metal (Se°) and a cyanide salt such as potassium cyanide, or added to the reaction mixture as it is.

Another implementation of the method is characterized in that the copper salt is a cuprous ($Cu^I$) salt, such as cuprous iodide.

A further implementation of the method is characterized in that the polar organic solvent is preferably dimethylformamide.

A further implementation of the method is characterized in that the oxidizing agent which is optionally used to oxidize the selenium is a peracid such as metachloroperbenzoic acid, or hydrogen peroxide.

Other aims, features and advantages of the invention will become clear from the following description which is made with reference to non limiting examples which are given by way of illustration and in no way limit the scope of the invention. In the examples, all the percentages are given as percentages by weight unless otherwise indicated.

EXPERIMENTAL SECTION

Figure 1:
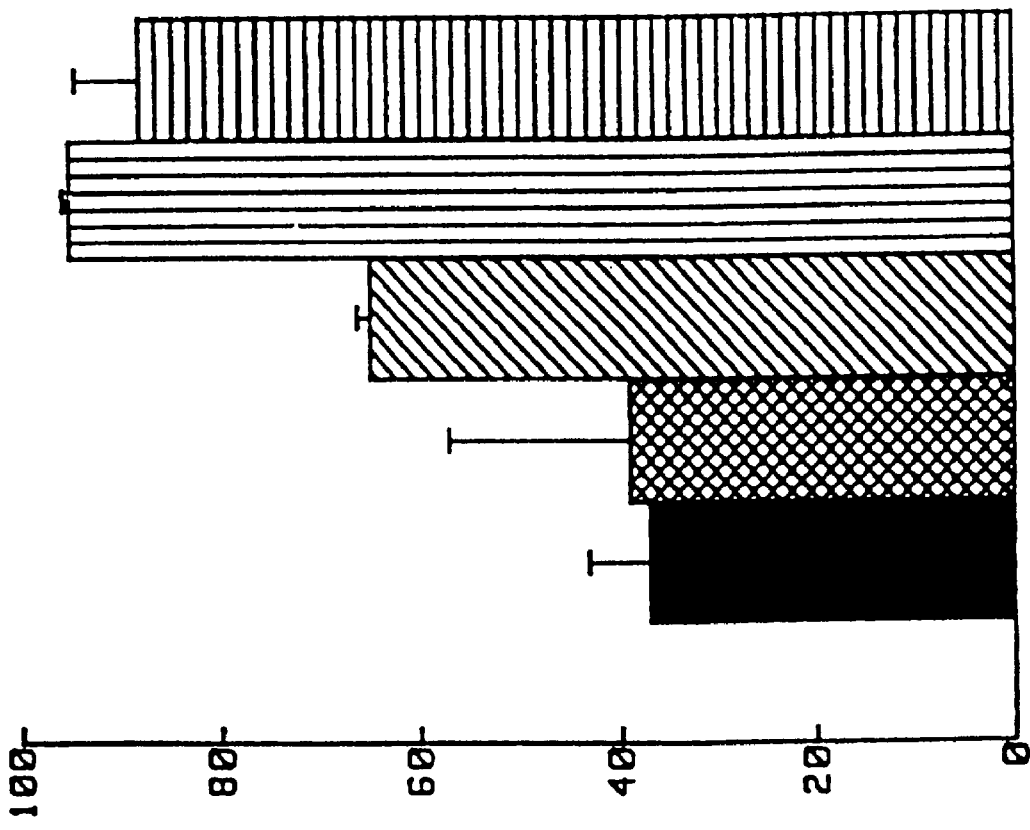
FIG. 1 shows a histogram of the results obtained during a viability test carried out on endothelial cells subjected to an oxidizing stress induced by the linoleic acid hydroperoxide with respect to a control. The reference is shown by the black rectangle. Various compounds of the invention, namely BXT-51056, BXT-51072 and BXT-51077, were used in the test described in Example 18.

All reactions were carried out in an inert nitrogen atmosphere unless otherwise stated.

Mass spectra were recorded using a Nermag R10-10B instrument. Ionisation used either electron impact (EI) at 70 electron volts, chemical ionisation (IC) in ammonia, butane or isobutane, or fast atom bombardment (FAB) using a glycerol matrix.

$^1H$ and $^{13}C$ NMR spectra were recorded using a Varian Gemini-200 instrument. Chemical displacements are expressed in ppm with respect to tetramethylsilane. Multiplicities are expressed as follows: "s" for singlet, "sl" for broad singlet, "d" for doublet, "t" for triplet, "q" for quadruplet and "m" for multiplet.

Melting points (MP° C.) were recorded using a Gallenkamp instrument and are uncorrected.

Purification by liquid column chromatography was carried out using Merck® $Si60F_{254}$ silica.

EXAMPLES OF SYNTHESIS OF COMPOUNDS WITH GENERAL FORMULA I:

Series when n=0 and $R^1=R^2$=hydrogen:

EXAMPLE 1

Preparation of 3,3-dimethyl-benzisoselenazoline: BXT-51056

A/ Preparation of 2-(2'-bromophenyl)-2-methylpropionitrile:

A solution of 2-(2'-bromophenyl)-acetonitrile (7.5 g; 38 mmole) and iodomethane (16.2 g; 114 mmole) in THF (30 ml) was slowly added (60 minutes) to a suspension of NaH (4.0 g; 100 mmole) in THF (100 ml) which had been refluxed in an inert atmosphere. The reaction was exothermic. Refluxing was continued for 2.5 h. The reaction mixture was then stirred at room temperature for 15 h. The solvent was evaporated off under reduced pressure; the residue was taken up in 100 ml of water and extracted with 2×100 ml of tertiobutylmethylether. The organic phases were combined, washed with 3×100 ml of a saturated NaCl solution; dried over $MgSO_4$ then filtered. The solvent was evaporated off under reduced pressure. The desired product was obtained as a colorless oil after distillation under reduced pressure (T*=125–140° C. ; p=0.1 mbar).

Yield=79%.

This substance was also made using the procedure described by W. E. Parham and L. D. Jones (see J. Org. Chem., (1976), 41, pp 1187–1191) with a yield of 90%.

Physical characteristics:

$^1H$ NMR ($CDCl_3$) 1.90 ppm (s; 6H); 7.19 ppm (m; 1H; J=7.5 Hz); 7.35 ppm (t; 1H; J=7.5 Hz); 7.49 ppm (m; 1H; J=7.5 Hz); 7.67 ppm (d; 1H; J=7.5 Hz).

$^{13}C$ NMR: ($CDCl_3$) 27.13 ppm; 37.64 ppm; 123.08 ppm; 123.92 ppm; 127.76 ppm; 128.49 ppm; 130.15 ppm; 136.18 ppm; 138.77 ppm.

MS (IE; 70 eV) 225/223 ($M^+$; 80%); 210/208 (100%); 183/181 (75%); 102 (20%).

B/ Preparation of 2-(2'-bromophenyl)-2-methyl-propionamide:

The preceding derivative (6.7 g; 30 mmole) was dissolved in ethanol (70 ml); a saturated solution of potassium carbonate (70 ml) was then added to the solution followed by careful addition of hydrogen peroxide (50% solution; 2×70 ml) at a temperature of 10–15° C. The reaction was exothermic. The reaction mixture was stirred at room temperature for 14 h. Dichloromethane (200 ml) was added to the reaction mixture and the latter was then decanted. The aqueous phase was extracted with 100 ml of dichloromethane. The organic phases were combined, washed with 3×200 ml of water, dried over $MgSO_4$ then filtered. The desired product obtained was in the form of a very viscous colorless oil, and was used unpurified for the next step.

Yield: 90%.

Physical characteristics:

$^1H$ NMR ($CDCl_3$) 1.67 ppm (s; 6H); 5.1–5.5 ppm (sl; 2H); 7.17 ppm (td; 1H; $J_d$=2.0 Hz, $J_t$=7.5 Hz); 7.36 ppm (td; 1H; $J_d$=2.0 Hz $J_t$=7.5 Hz); 7.52 ppm (dd; 1H; J=2.0–7.5 Hz); 7.63 ppm (dd; 1H; J=2.0–7.5 Hz).

$^{13}$C NMR: (CDCl$_3$) 26.92 ppm; 48.78 ppm; 124.89 ppm; 128.34 ppm;
128.50 ppm; 129.42 ppm; 135.63 ppm; 143.84 ppm; 179.95 ppm.

MS (IE; 70 eV) 244/242 (MH$^+$; 3%); 225/223 (5%); 210/208 (10%); 171/169 (30%); 162 (100%); 145 (10%); 115 (30%); 91 (30%); 77 (25%).

C/ Preparation of 1-(2'-bromophenyl)-1-methyl-ethylamine:

The preceding derivative, dissolved in a water/acetonitrile mixture (50/50, 60 ml), was added all at once to bis (trifluoroacetoxy)iodosobenzene (10.88 g; 25.3 mmole). The reaction mixture was stirred at room temperature for 24 h. After addition of water (450 ml), stirring was continued for 30 min more. Tertiobutylmethylether (150 ml) was added to the reaction mixture and the latter was decanted. The organic phase was extracted with a 10% hydrochloric acid solution then the aqueous phase was washed with 3×150 ml of tertiobutylmethylether. The aqueous phase was alkalinised (12<pH<14) at 10° C. then extracted with 3×150 ml of dichloromethane. The organic phases were combined, dried over MgSO$_4$ then filtered. The desired product was obtained in the form of a very viscous colorless oil after distillation (T*=60–70° C. ; p=0.1 mbar).
Yield: 83%.
Physical characteristics:
$^1$H NMR (CDCl$_3$) 25 1.65 ppm (s; 6H); 2.15 ppm (sl; 2H); 7.05 ppm (td; 1H; J$_d$=2.0 Hz, J$_t$=7.5 Hz); 7.25 ppm (td; 1H; J$_d$=2.0 Hz J$_t$=7.5 Hz); 7.57 ppm (m; 2H).
$^{13}$C NMR: (CDCl$_3$) 30.71 ppm; 54.17 ppm; 122.22 ppm; 127.76 ppm; 127.97 ppm; 128.56 ppm; 136.12 ppm; 147.75 ppm.

MS: (IE; 70 eV) 216/214 (MH$^+$, 2%); 200/198 (100%); 58 (98%).

MS: (IC; butane) 216/214 (MH$^+$; 100%); 199/197 (20%); 154 (25%); 93 (30%).

D/ Preparation of 3,3-dimethyl-benzisoselenazoline: BXT-51056.

Triethylamine (3.13 ml; 37.5 mmole), then potassium selenocyanate (1.19 g; 8.25 mmole) and copper iodide CuI (1.49 g; 7.5 mmole) were added to a solution of the preceding derivative (1.605 g; 7.5 mmole) in DMF (35 ml). The reaction mixture was stirred at room temperature for 18 h, then poured into 150 ml of water. The suspension obtained was filtered and washed with 150 ml of ethyl acetate. After decanting, the aqueous phase was extracted with 2×150 ml of ethyl acetate. The organic phases were combined, washed with 2×100 ml of a saturated NaCl solution, dried over MgSO$_4$ then filtered. The solvent was evaporated off under reduced pressure. The desired product was obtained after purification by liquid chromatography on a silica column (eluent: cyclohexane-ethyl acetate, 5/1).
Yield: 64%.
Physical characteristics:
MP° C.: 38.5–39.5° C. (corrected) $^1$H NMR (CDCl$_3$) 1.55 ppm (s; 6H); 4.10 ppm (sl; 2H); 7.05 ppm (m; 1H); 7.18 ppm (m; 2H); 7.30 ppm (m; 1H). (acetone d$_6$) 1.48 ppm (s; 6H); 4.70 ppm (sl; 1H) 7.05–7.25 ppm (m; 3H); 7.40 ppm (m; 1H). (DMSO d$_6$) 1.40 ppm (s; 6H); 5.25 ppm (sl; 1H); 7.00–7.20 ppm (m; 3H); 7.45 ppm (m; 1H).
$^{13}$C NMR: (acetone d$_6$) 26.63 ppm; 71.29 ppm; 124.31 ppm; 125.08 ppm; 126.68 ppm; 128.61 ppm; 140.57 ppm; 150.85 ppm.

MS: (IE; 70 eV) 213 (M$^+$; 20%); 198 (100%); 157 (25%); 80 (20%).

EXAMPLE 2

Preparation of 2-acetyl-3,3-dimethyl-benzisoselenazoline: BXT-51057

The derivative 3,3-dimethyl-benzisoselenazoline (148 mg; 0.7 mmole) was dissolved at room temperature in ethyl ether (4 ml). Triethylamine (107 μl; 0.77 mmole) and acetyl chloride (54 μl; 0.77 mmole) were added. A white precipitate appeared immediately. After 1 h, 1 ml of water was added to the reaction mixture. The crude product was extracted with 3×20 ml of dichloroethane. The organic phases were combined, washed with 2×20 ml of a saturated NaCl solution, dried over MgSO$_4$ then filtered. The solvent was evaporated off under reduced pressure. The desired product was obtained after purification by liquid chromatography on a silica column (eluent: cyclohexane-ethyl acetate, 1/1).
Yield: 26%.
Physical characteristics: MP° C.: 91–92° C. (corrected) $^1$H NMR (CDCl$_3$) 1.79 ppm (s; 6H); 2.32 ppm (sl; 3H); 7.00 ppm (m; 1H); 7.05–7.20 ppm (m; 3H). (acetone d$_6$) 1.80 ppm (s; 6H); 2.25 ppm (sl; 3H); 7.15–7.35 ppm (m; 3H) 7.43 ppm (m; 1H). $^{13}$C NMR: (acetone d$_6$) 22.0 ppm; 27.7 ppm; 67.0 ppm; 123.79 ppm; 125.75 ppm; 127.35 ppm; 129.63 ppm; 132.61 ppm; 149.13 ppm; 169.06 ppm.

MS: (IE; 70 eV) 255 (M$^+$; 30%); 240 (30%); 198 (100%).

EXAMPLE 3

Preparation of 3,3-dimethyl-2-ethyl-benzisoselenazoline: BXT-51058

Diazabicycloundecene (380 mg; 2.5 mmole) was added to a solution of derivative 3,3-dimethyl-benzisoselenazoline (107 mg; 0.5 mmole) obtained above in bromoethane (1.5 ml). The mixture was stirred at room temperature for 10 h, then the same quantity of diazabicycloundecene was added again. After 14 h at room temperature, the bromoethane was evaporated off under reduced pressure. The desired product was obtained in the form of a very viscous yellow oil after purification by liquid chromatography on a silica column (eluent: cyclohexane-ethyl acetate, 6/1).
Yield: 53%.
Physical characteristics:
$^1$H NMR (CDCl$_3$) 1.16 ppm (t; 3H; J=7.0 Hz); 1.56 ppm (s; 6H); 2.84 ppm (q; 2H; J=7.0 Hz); 7.05 ppm (m; 1H); 7.18 ppm (m; 2H); 7.20 ppm (m; 1H).
$^{13}$C NMR: (CDCl$_3$) 16.78 ppm; 25.33 ppm; 47.82 ppm; 73.27 ppm; 124.01 ppm; 124.90 ppm; 126.29 ppm; 128.22 ppm; 136.29 ppm; 148.47 ppm. MS (IE; 70 eV) 241 (M$^+$; 30%); 226 (100%); 198 (30%); 157 (10%); 115 (10%).

EXAMPLE 4

Preparation of 3,3-dimethyl-benzisoselenazoline-1-oxide: BXT-51088

The derivative 3,3-dimethyl-benzisoselenazoline BXT-51056 (212 mg; 1 mmole) was dissolved at room temperature in methanol (5 ml) with stirring. After addition of 5% hydrogen peroxide (600 μl; 1.05 mmole), stirring was continued for 15 min. The solvent was evaporated off under reduced pressure. The residue was taken up in 25 ml of dichloromethane and washed with 3×3 ml of a saturated NaCl solution, dried over Na$_2$SO$_4$ then filtered. After evaporation of the solvent under reduced pressure, the desired product was obtained in the form of yellowish crystals.
Yield: 55%.
Physical characteristics:
$^1$H NMR (CDCl$_3$) 1.54 ppm (sl; 3H); 1.72 ppm (sl; 3H); 4.35 ppm (sl; 1H); 7.32 ppm (d; 1H; J=8.0 Hz); 7.50 ppm (m; 2H; 7.76 ppm (d; 1H; J=8.0 Hz).
$^{13}$C NMR: (CDCl$_3$) 30.98 ppm; 35.20 ppm; 71.40 ppm; 124.59 ppm; 126.62 ppm; 129.35 ppm; 132.29 ppm; 145.16 ppm; 151.73 ppm.

MS: (FAB) 230 (MH+; 100%); 154 (90%); 136 (70%).
Series where n=0 and R1≠hydrogen

EXAMPLE 5

3,3'-dimethyl-7-nitro-benzisoselenazoline: BXT-51062

A/ Preparation of (2'-bromo-3'-nitro)-phenylacetonitrile:

This compound was prepared using conventional methods, from 2-bromo-3-nitrotoluene by monohalogenation to produce 2-bromo-3-nitrobromobenzyl (see A. Ricci et al., Ann. Chim. (Rome); (1963); 53, p 1860) then by substitution using potassium cyanide to obtain (2'-bromo-3'-nitro)-phenylacetonitrile (see J. Weinstock et al., J. Med. Chem., (1987), 30, p 1166).

Overall yield of these two steps: 43%.

Physical characteristics:

MP° C.: 122–123° C. (corrected)

1H NMR: (CDCl$_3$) 3.95 ppm (s; 2H); 7.55 ppm (t; 1H; J=8 Hz); 7.76 ppm (m; 2H) $^{13}$C NMR: (CDCl$_3$) 25.78 ppm; 115.84 ppm; 116.52 ppm; 125.44 ppm; 129.37 ppm; 139.10 ppm; 143.87 ppm; 152.01 ppm. MS (IE; 70 eV) 242/240 (M+; 70%); 212/210 (20%); 193/191 (30%); 115 (100%); 103 (50%); 88 (30%).

B/ Preparation of 2-(2'-bromo-3'-nitro)-phenyl-2-methylpropionitrile

The desired derivative was obtained using a similar procedure to that described in Example 1/A.

Yield: 70%

Physical characteristics:

MP° C.: 99–100° C. (corrected)

1H NMR: (CDCl$_3$) 1.95 ppm (s; 6H); 7.45–7.70 ppm (m; 3H).

MS: (IE; 70 eV) 270/268 (M+; 80%); 255/253 (100%); 228/226 (40%); 143 (20%); 127 (25%); 115 (30%); 61 (40%).

C/ Preparation of 2-(2'-bromo-3'-nitro)-phenyl-2-methylpropionamide

The desired derivative was obtained using a similar procedure to that described in Example 1/B.

Yield: 77%

Physical characteristics:

MP° C.: 123° C. (corrected)

1H NMR: (CDCl$_3$) 1.73 ppm (s; 6H); 5.40 ppm (sl; 2H); 7.45–7.57 ppm (m; 2H); 7.70 ppm (m; 1H).

MS: (IC; butane) 289/287 (M+; 100%); 207 (15%).

Preparation of 1-(2'-bromo-3'-nitro)-phenyl-1-methylethylamine

The desired derivative was obtained using a similar procedure to that described in Example 1/C.

Yield: 57%

Physical characteristics:

1H NMR: (CDCl$_3$) 1.70 ppm (s; 6H); 1.90 ppm (sl; 2H); 7.40 ppm (m; 2H); 7.85 ppm (m; 1H).

E/ Preparation of 3,3'-dimethyl-7-nitro-benzisoselenazoline: BXT-51062

The desired derivative was obtained using a similar procedure to that described in Example 1/D.

Yield: 45%

Physical characteristics:

MP° C.: 121° C. (corrected)

1H NMR: (CDCl$_3$) 1.55 ppm (s; 6H); 3.75 ppm (sl; 1H); 7.25–7.43 ppm (m; 2H); 8.19 ppm (m; 1H).

1H NMR: (acetone d$_6$) 1.55 ppm (s; 6H); 4.65 ppm (sl; 1H); 7.46–7.60 ppm (m; 2H); 8.19 ppm (m; 1H) $^{13}$C NMR: (acetone d$_6$) 27.06 ppm; 71.43 ppm; 124.05 ppm; 128.84 ppm; 129.48 ppm; 137.18 ppm.

MS: (IE; 70 eV) 258 (M+; 20%); 243 (100%); 197 (40%); 117 (10%).

EXAMPLE 6

3,3'-dimethyl-5-nitro-benzisoselenazoline: BXT-51075

A/ Preparation of 2-(2'-bromo-5'-nitro)-phenyl-2-methylpropionitrile

This compound was prepared using a procedure which was very similar to that of the derivative of Example 1/A and was obtained in the form of a yellow solid.

Yield: 80%

Physical characteristics:

MP° C.: 96° C. (corrected)

1H NMR: (CDCl$_3$) 1.95 ppm (s; 6H); 7.89 ppm (d; 1H; J=9.0 Hz); 8.08 ppm (dd; 1H; J=2.5–9.0 Hz); 8.32 ppm (d; 1H; J=2.5 Hz).

B/ Preparation of 2-(2'-bromo-5'-nitro)-phenyl-2-methylpropionamide

The preceding compound was hydrolysed using a procedure which was very similar to that of the derivative of Example 1/B to produce the desired compound in the form of a very pale yellow powder.

Yield: 56%

Physical characteristics:

MP° C.: 206° C. (corrected)

1H NMR: (CDCl$_3$) 1.74 ppm (s; 6H); 5.35 ppm (sl; 2H); 7.82 ppm (d; 1H; J=8.5 Hz); 8.30 ppm (dd; 1H; J=2.5–8.5 Hz); 8.37 ppm (d; 1H; J=2.5 Hz).

MS: (IC; isobutane) 289/287 (MH+; 100%); 207 (15%).

C/ Preparation of 2-(2'-bromo-5'-nitro)-phenyl-1-methylethylamine

This compound was prepared using a procedure which was very similar to that for the derivative of Example 1/C and was obtained in the form of a pale yellow powder.

Yield: 83%

Physical characteristics:

MP° C.: 105–106° C. (corrected)

1H NMR: (CDCl$_3$) 1.71 ppm (s; 6H); 1.90 ppm (sl; 2H); 7.77 ppm (d; 1H; J=9.0 Hz); 7.93 ppm (dd; 1H; J=3.0–9.0 Hz); 8.57 ppm (d; 1H; J=3.0 Hz). $^{13}$C NMR: (CDCl$_3$) 30.41 ppm; 54.49 ppm; 122.99 ppm; 123.12 ppm; 129.36 ppm; 137.07 ppm; 147.66 ppm (1); 150.14 ppm.

MS: (IC; isobutane) 261/259 (MH+; 100%).

D/ Preparation of 3,3-dimethyl-5-nitro-benzisoselenazoline

This compound was prepared using a procedure which was very similar to that for the derivative of Example 1/D and was obtained in the form of yellow crystals.

Yield: 61%

Physical characteristics:

MP° C.: 107° C. (corrected)

1H NMR: (CDCl$_3$) 1.56 ppm (s; 6H); 4.20 ppm (sl; 1H); 7.44 ppm (d;

1H; J=8.5 Hz); 7.83 ppm (d; 1H; J=2.0 Hz); 8.08 ppm (dd; 1H; J=2.0–8.5 Hz). $^{13}$C NMR: (CDCl$_3$) 26.48 ppm; 70.86 ppm; 118.39 ppm; 123.72 ppm; 124.39 ppm; 147.48 ppm (1); 149.91 ppm; 151.65 ppm.

MS: (IC; isobutane) 259 (MH+; 100%).

EXAMPLE 7

Preparation of 3,3-dimethyl-7-fluoro-benzisoselenazoline: BXT-51076

A/ Preparation of 2-(3'-amino-2'bromo)-phenyl-2-methyl-propionitrile

The compound obtained in Example 4/B was reduced with tin (II) chloride to produce the desired derivative in the form of a brown solid which was used unpurified in the following step.

Yield: 94%

Physical characteristics:

$^1$H NMR: (CDCl$_3$) 1.87 ppm (s; 6H); 4.30 ppm (sl; 2H); 6.79 ppm (m; 2H); 7.11 ppm (t; 1H; J=8.0 Hz).

MS: (IE; 70 eV) 240/238 (M$^+$; 100%); 225/223 (25%); 198/196 (30%); 144 (20%); 117 (20%).

B/ Preparation of 2-bromo-3-(2'-methyl-2'propionitrilo)-benzenediazonium hexafluorophosphate The preceding derivative (1.54 g; 6.44 mmole) was dissolved at room temperature in a solution constituted by concentrated hydrochloric acid (2.7 ml) diluted in 20 ml of water. Sodium nitrite (533 mg; 7.73 mmole) was added with stirring at a temperature of 0–5° C. After 5 min, lithium hexafluorophosphate (1.66 g; 10.95 mmole) was also added. A white precipitate appeared immediately. After 30 min, the suspension obtained was filtered and washed with 8 ml of cold water, then with 9 ml of a mixture of tertiobutylmethylether and methanol (2:1). The desired compound was obtained in the form of a colorless powder which was used unpurified in the next step.

Yield: 86%

Physical characteristics:

MP° C.: 127° C. (dec)

$^1$H NMR: (acetone d$_6$) 2.05 ppm (s; 6H); 8.23 ppm (m; 1H); 8.60 ppm (m; 1H); 9.03 ppm (m; 1H).

C/ Preparation of 2-(2'-bromo-3'-fluoro )-phenyl-2-methylpropionitrile

This compound was prepared by the Schiemann method by pyrolysis of the preceding compound (5×300 mg; 3.78 mmole), mixed with potassium fluoride (5×300 mg), with no solvent and in a vacuum (0.1 mbar). The desired product was obtained in the form of a light brown powder.

Yield: 30%

Physical characteristics:

MP° C.: 39° C. (corrected)

$^1$H NMR: (CDCl$_3$) 1.91 ppm (s; 6H); 7.15 ppm (td; 1H; J$_d$=2.0 Hz; J$_t$=8.0 Hz); 7.23–7.41 ppm (m; 2H).

MS: (IE; 70 eV) 243/241 (M$^+$; 80%); 228/226 (100%); 201/199 (80%); 120 (30%).

D/ Preparation of 2-(2'-bromo-3'-fluoro)-phenyl-2-methylpropionamide

The preceding compound was hydrolysed using a procedure which was very similar to that for the derivative of Example 1/B, to produce the desired compound, in the form of colorless crystals.

Yield: 76%

Physical characteristics:

MP° C.: 140° C. (corrected)

$^1$H NMR: (CDCl$_3$) 1.69 ppm (s; 6H); 5.15–5.35 ppm (sl; 2H); 7.10 ppm (m; 1H); 7.23–7.41 ppm (m; 2H).

MS: (IC; isobutane) 262/260 (MH+; 100%); 180 (20%).

E/ Preparation of 1-(2'-bromo-3'-fluoro)-phenyl-1-methylethylamine

This compound was prepared using a very similar procedure to that for the derivative of Example 1/C and was obtained in the form of a colorless oil.

Yield: 72%

Physical characteristics:

$^1$H NMR: (CDCl$_3$) 1.67 ppm (s; 6H); 1.90 ppm (sl; 2H); 7.03 ppm (td; 1H; J$_d$=2.0 Hz; J$_t$=8.0 Hz); 7.24 ppm (td; 1H; J$_d$=5.5 Hz, J$_t$=8.0 Hz); 7.39 ppm (m; 1H; J=8.0 Hz).

MS: (IC; isobutane) 234/232 (MH$^+$; 100%).

F/ Preparation of 3,3-dimethyl-7-fluoro-benzisoselenazoline

This compound was prepared using a very similar procedure to that for the derivative of Example 1/D and was obtained in the form of yellowish crystals.

Yield: 52%

Physical characteristics:

MP° C.: 25° C. (corrected)

$^1$H NMR: (CDCl$_3$) 1.50 ppm (s; 6H); 4.05 ppm (sl; 1H); 6.82 ppm (d; 1H; J=7.5 Hz); 6.92 ppm (td; 1H; J$_d$=1.0 Hz; J$_t$=7.5 Hz); 7.16 ppm (td; 1H; J$_d$=5.0 Hz; J$_t$=7.5 Hz).

MS: (IE; 70 eV) 231 (M$^+$; 30%); 216 (100%); 175 (25%).

Series where n=1 and R$^1$=R$^2$=hydrogen

EXAMPLE 8

Preparation of 4,4-dimethyl-benzisoselenazine: BXT-51072

A/ Preparation of 2-(2'-bromophenyl)-2-methylpropylamine

The derivative 2-(2'-bromophenyl)-2-methylpropionitrile from Example 1/A (2.24 g; 10 mmole) was dissolved in THF (25 ml) in an inert atmosphere. A solution of borane BH$_3$ in THF (1 M; 25 ml; 25 mmole) was slowly added to the reaction medium. The new solution obtained was refluxed for 3 h. After cooling to room temperature, an aqueous solution of trifluoroacetic acid (50 ml; 1/1) was added dropwise to the reaction mixture. The mixture was refluxed for 1 h, then the solvents were evaporated off under reduced pressure. The residue was taken up in 60 ml of hydrochloric acid HCl (10%) and washed with 3×100 ml of ethyl acetate. The aqueous phase was alkalinised (12<pH<14) then extracted with 3×50 ml of dichloromethane. The organic phases were combined, washed with 2×100 ml of a saturated NaCl solution, dried over MgSO$_4$ then filtered. The solvent was evaporated off under reduced pressure. The desired compound was obtained as a yellowish oil.

Yield: 60%

Physical characteristics:

$^1$H NMR: (CDCl$_3$) 1.40 ppm (sl; 6H); 1.44 ppm (s; 6H); 3.19 ppm (s; 2H); 7.03 ppm (td; 1H; J$_d$=2.0 Hz; J$_t$=8.0 Hz); 7.24 ppm (td; 1H; J$_d$=1.5 Hz; J$_t$=8.0 Hz) 7.38 ppm (dd; 1H; J=2.0–8.0 Hz); 7.57 ppm (dd; 1H; J=1.5–8.0 Hz). $^{13}$C NMR: (CDCl$_3$) 26.59 ppm; 42.43 ppm; 50.73 ppm; 122.76 ppm; 127.87 ppm; 128.46 ppm; 130.62 ppm; 136.42 ppm; 144.79 ppm.

MS: (IC; isobutane) 230/228 (MH+; 100%); 148 (30%).

B/ Preparation of 4,4-dimethyl-benzisoselenazine

This compound was obtained using a very similar procedure to that of the derivative of Example 1/D, in the form of colorless crystals.

Yield: 20%

Physical characteristics:

MP° C.: 81° C. (corrected)

$^1$H NMR: (CDCl$_3$) 1.28 ppm (s; 6H); 3.25 ppm (s; 2H); 3.45 ppm (sl; 1H); 6.98–7.14 ppm (m; 3H); 7.43 ppm (m; 1H). $^{13}$C NMR: (CDCl$_3$) 28.46 ppm; 33.02 ppm; 61.41 ppm; 125.21 ppm; 125.94 ppm; 126.83 ppm; 127.97 ppm; 129.87 ppm; 143.26 ppm.

MS: (IE; 70 eV) 227 (M$^+$; 85%); 198 (80%); 183 (100%); 132 (30%); 117 (50%); 102 (20%); 91 (25%).

EXAMPLE 9

Preparation of 4,4-dimethyl-benzisoselenazine-1-oxide: BXT-51089

The desired derivative was obtained from 4,4-dimethyl-benzisoselenazine BXT-51072 by a similar procedure to that described for Example 4.

Yield: 84%

Physical characteristics:

$^1$H NMR: (CDCl$_3$) 1.34 ppm (s; 3H); 1.37 ppm (s; 3H); 2.79 ppm (d; 1H; J=14 Hz); 3.3 ppm (sl; 1H); 3.98 ppm (d; 1H; J=14 Hz); 7.28 ppm (m; 1H); 7.36 ppm (m; 3H). (D$_2$O) 1.29 ppm (s; 3H); 1.37 ppm (s; 3H); 2.96 ppm (d; 1H; J=14

Hz); 3.65 ppm (d; 1H; J=14 Hz); 7.42 ppm (m; 1H); 7.60 ppm (m; 2H); 7.74 ppm (m; 1H). $^{13}$C NMR: (D$_2$O) 28.43 ppm; 30.73 ppm; 36.79 ppm; 49.88 ppm; 130.53 ppm; 131.06 ppm; 132.52 ppm; 135.97 ppm; 137.04 ppm; 148.08 ppm.

MS: (FAB) 244 (MH$^+$; 100%); 154 (50%); 136 (38%).

EXAMPLE 10

Preparation of 4,4-dimethyl-2-ethyl-benzisoselenazine: BXT-51078

A/ Preparation of N-[2-(21-bromophenyl)-2-methylpropyl]-N-ethylamine

Iodoethane (146 mg; 75 μl; 1 mmole) was added to the derivative 2-(2'-bromophenyl)-2-methylpropylamine from Example 7/A (228 mg; 1 mmole). The reaction mixture was stirred at room temperature. After 30 min, a white precipitate appeared and after 60 min, 500 μl of chloroform was added. Stirring was continued for 1 h. Dichloromethane (40 ml) and a saturated NaHCO$_3$ solution (20 ml) were added to the reaction medium, and the latter was then decanted. The organic phase was washed with 20 ml of a saturated NaCl solution, dried over MgSO$_4$ then filtered. The solvent was evaporated off under reduced pressure. The desired product was obtained in the form of a yellowish oil, mixed with 12% of the starting substance (II) and 12% of N-[2-(2'-bromophenyl)-2-methylpropyl]-N,N-diethylamine (III). This mixture was used unpurified in the next step.

Crude yield: 76%.

Physical characteristics:

$^1$H NMR: (CDCl$_3$) (mixture of desired product (I), II and III; 76/12; 12) I; 1.03 ppm (t; 3H; J=7 Hz); 1.52 ppm (s; 6H); 2.62 ppm (q; 2H; J=7 Hz); 3.13 ppm (s; 2H); 7.06 ppm (m; 1H); 7.28 ppm (m; 1H); 7.45 ppm (m; 1H); 7.60 ppm (m; 1H). II: 2-(2'-bromophenyl)-2-methylpropylamine from Example 7/A. III: 0.85 ppm (t; 6H; J=7 Hz); 2.39 ppm (q; 4H; J=7 Hz); 3.22 ppm (s; 2H).

MS: (IC; isobutane) 258/256 (M$^+$; 100%).

B/ Preparation of 4,4-dimethyl-2-ethyl-benzisoselenazine

This compound was obtained using a procedure which was very similar to that for the derivative of Example 1/D from the preceding derivative, in the form of a yellow oil.

Yield: 20%

Physical characteristics:

$^1$H NMR: (CDCl$_3$) 1.19 ppm (t; 3H; J=7 Hz); 1.35 ppm (s; 6H); 2.92 ppm (q; 2H; J=7 Hz); 3.16 ppm (s; 2H); 7.07 ppm (m; 3H); 7.43 ppm (m; 1H). $^{13}$C NMR: (CDCl$_3$) 14.63 ppm; 30.26 ppm; 36.39 ppm; 54.69 ppm; 69.93 ppm; 126.13 ppm; 126.67 ppm; 126.76 ppm; 127.93 ppm; 129.34 ppm; 143.64 ppm.

MS: (IC; isobutane) 256 (MH$^+$; 100%).

Series in which n=1 and R$^1$≠hydrogen

EXAMPLE 11

Preparation of 4,4-dimethyl-6-methoxy-benzisoselenazine: BXT-51077

A/ Preparation of 5-amino-2-bromo-phenylacetonitrile 2-(2'-bromo-5'-nitro)-phenylacetonitrile (1.65 g; 6.85 mmole) was reduced using tin (II) chloride using the procedure described by F. Bellamy et al., (see Tetrahedron Let., (1984), 25, 8, pp 839–842) to produce the desired derivative, which was obtained in the form of a yellowish powder.

Yield: 69%

Physical characteristics:

MP° C.: 100° (corrected)

$^1$H NMR: (CDCl$_3$) 3.75 ppm (s; 2H); 3.80 ppm (sl; 2H); 6.53 ppm (dd; 1H; J=2.5–8.5 Hz); 6.85 ppm (d; 1H; J=2.5 Hz); 7.31 ppm (d; 1H; J=8.5 Hz).

MS: (IE; 70 eV) 210/212 (M$^+$; 100); 131 (60); 104 (25); 77 (20).

B/ Preparation of 2-bromo-5-hydroxy-phenylacetonitrile

The preceding derivative (1 g; 4.74 mmole) was dissolved in sulfuric acid (35%; 20 ml) and a solution of sodium nitrite (409 mg; 6 mmole) in water (5 ml) was added at a temperature of 0° C. After 5 min, a solution of copper (II) nitrate (17.2 g; 71 mmole) in water (100 ml) was added, followed by solid copper (I) oxide (678 mg; 4.74 mmole). The reaction mixture was stirred at room temperature for 2 h, then extracted with 3×100 ml of tertiobutylmethylether. The organic phases were combined, then extracted with 2×100 ml of sodium hydroxide NaOH (1N). The aqueous phases were combined, acidified (pH=2), then extracted with 3×100 ml of dichloromethane. The organic phases were combined, dried over MgSO$_4$ then filtered. The desired product was obtained in the form of a brown powder which was used unpurified in the next step.

Yield: 69%

Physical characteristics:

$^1$H NMR: (CDCl$_3$) 3.81 ppm (s; 2H); 5.70 ppm (sl; 2H); 6.74 ppm (dd; 1H; J=2.5–8.5 Hz); 7.08 ppm (d; 1H; J=2.5 Hz); 7.44 ppm (d; 1H; J=8.5 Hz).

MS: (IE; 70 eV) 213/211 (M$^+$; 100); 132 (98); 104 (20); 77 (30).

C/ Preparation of 2-(2'-bromo-5'-methoxy)-phenyl-2-methylpropionitrile

A solution composed of the preceding derivative (670 mg; 3.16 mmole) and iodomethane (2.7 g; 19 mmole) in DMF (15 ml) was slowly added (6 min) to a suspension of sodium hydride NaH (60%; 506 mg; 12.64 mmole) in DMF (15 ml) at a temperature of 0° C. Stirring was continued for 10 min at this temperature, then for 2 h at room temperature. The reaction mixture was carefully poured into 50 ml of water and extracted with 2×50 ml of ethyl acetate. The organic phases were combined, washed with 50 ml of a saturated NaCl solution, dried over MgSo$_4$ then filtered. The solvent was evaporated off under reduced pressure. The desired product was obtained in the form of yellow crystals after purification by liquid chromatography on a silica column (eluent: cyclohexane-ethyl acetate, 4/1).

Yield: 83%

Physical characteristics:

MP° C.: 43° C. (corrected)

$^1$H NMR: (CDCl$_3$) 1.87 ppm (s; 6H); 3.81 ppm (s; 3H); 6.75 ppm (dd; 1H; J=3.0–8.5 Hz); 7.04 ppm (d; 1H; J=3.0 Hz); 7.55 ppm (d; 1H; J=8.5 Hz).

MS: (IE; 70 eV) 255/253 (M$^+$; 100); 240/238 (40); 213/211 (50); 132 (20).

D/ Preparation of 2-(2'-bromo-5'-methoxy)-phenyl-2-methylpropylamine

The preceding derivative (386 mg; 1.5 mmole) was dissolved in an inert atmosphere in THF (15 ml). A solution of borane in THF (1 M; 3.75 ml; 3.75 mmole) was slowly added. The reaction mixture was refluxed for 3 h. After cooling to room temperature, acetic acid (90% solution; 2 ml) was carefully added. The mixture was again refluxed, this time for 30 min, then poured into 50 ml of a hydrochloric acid HCl solution (1 N) and washed with 3×50 ml of tertiobutylmethylether. The aqueous phase was alkalinised (12<pH<14) then extracted with 2×50 ml of dichloromethane. The organic phases were combined, washed with 50 ml of a saturated NaCl solution, dried over MgSO$_4$ then filtered. The solvent was evaporated off under reduced pressure. The desired product was obtained as a yellow oil.

Yield: 78%

Physical characteristics:
 $^1$H NMR: (CDCl$_3$) 1.35 ppm (sl; 2H); 1.45 ppm (s; 6H); 3.20 ppm (s; 2H); 3.79 ppm (s; 3H); 6.62 ppm (dd; 1H; J=3.0–8.5 Hz); 6.97 ppm (d; 1H; J=3.0 Hz); 7.49 ppm (d; 1H; J=8.5 Hz).
 MS: (IC; isobutane) 260/258 (MH+; 100); 178 (80).

E/ Preparation of 4,4-dimethyl-6-methoxy-benzisoselenazine

This compound was obtained, using a very similar procedure to that for the derivative of Example 1/D, in the form of pale yellow needles.
Yield: 42%
Physical characteristics:
 MP° C.: 86° C. (corrected)
 $^1$H NMR: (CDCl$_3$) 1.27 ppm (s; 6H); 3.23 ppm (s; 2H); 3.40 ppm (sl; 1H); 3.78 ppm (s; 3H); 6.69 ppm (dd; 1H; J=2.5–8.0 Hz); 6.93 ppm (d; 1H; J=8.0 Hz); 7.03 ppm (d; 1H; J=2.5 Hz). $^{13}$C NMR: (CDCl$_3$) 28.60 ppm; 33.40 ppm; 55.64 ppm; 61.50 ppm; 112.54 ppm; 114.59 ppm; 119.90 ppm; 126.03 ppm; 144.49 ppm; 158.31 ppm.
 MS: (IE; 70 eV) 257 (M$^+$; 100); 228 (80); 213 (75); 197 (20); 148 (20).

EXAMPLE 12

Preparation of 4,4-dimethyl-6-(2'-(4"-methylpiperazine-1"-yl)ethoxybenzisoselenazine: BXT-51080

A/ Preparation of 2-(2'-bromo-5'-hydroxy)-phenyl-2-methylpropylamine

The 2-(2'-bromo-5'-methoxy)-phenyl-2-methylpropylamine derivative of Example 11/D (3.0 g; 11.6 mmole) was dissolved in an inert atmosphere in dichloromethane (11.6 ml). A solution of boron tribromide in dichloromethane (1M; 23.2 mmole) was slowly added to the reaction medium at a temperature of 0° C. Stirring was continued for 15 min at this temperature then for 45 min at room temperature. After cooling to 0° C., water (20 ml) was carefully added. The reaction mixture was neutralised by addition of potassium bicarbonate. The precipitate obtained was filtered and washed with water (10 ml) then with tertiobutylmethylether (10 ml). The desired product was obtained, after drying, in the form of a light brown-gray powder which was used unpurified in the next step.
Yield: 80%
Physical characteristics:
 $^1$H NMR: (CD$_3$OD) 1.56 ppm (s; 6H); 3.56 ppm (sl; 2H); 6.65 ppm (dd; 1H; J=9–3 Hz); 6.85 ppm (d; 1H; J=3 Hz); 7.43 ppm (d; 1H; J=9 Hz). (DMSO-d$_6$) 1.48 ppm (s; 6H); 3.34 ppm (s; 2H); 3.4 ppm (sl; 2H); 6.67 ppm (dd; 1H; J=9–3 Hz); 6.93 ppm (d; 1H; J=3 Hz); 7.41 ppm (d; 1H; J=9 Hz); 7.80 ppm (sl; 1H). $^{13}$C NMR: (DMSO-d$_6$) 25.69 ppm; 38.85 ppm; 46.29 ppm; 109.85 ppm; 116.18 ppm; 117.69 ppm; 136.58 ppm; 142.86 ppm; 157.44 ppm.
 MS: (IC; isobutane) 246/244 (MH+; 100%); 166 (70%).

B/ Preparation of N-2-(2'-bromo-5'-hydroxyphenyl)-2-methylpropyl-N-(tert-butyloxycarbonyl)-amine The preceding derivative (340 mg; 1.4 mmole) was dissolved in a sodium hydroxide solution (1 N; 7 ml) at room temperature. Ditert-butyl dicarbonate (670 mg; 3 mmole) was added; the reaction mixture was then vigorously stirred for 1.5 h at a temperature of 35° C. Methanol (8 ml) followed by a concentrated sodium hydroxide solution (1.12 ml) were then added and the homogeneous solution was heated for 1 h at 85° C. The methanol was evaporated off under reduced pressure then the aqueous residue was neutralised. The precipitated was filtered, washed with water (20 ml) then dried. The desired product was thus obtained as a gray powder and used unpurified in the next step.
Yield: 56%
Physical characteristics:
 $^1$H NMR: (CDCl$_3$) 1.39 ppm (s; 6H); 1.41 ppm (s; 9H); 3.69 ppm (d; 2H; J=7 Hz); 4.30 ppm (t; 1H; J=7 Hz); 6.59 ppm (dd; 1H; J=9–2.5 Hz); 6.90 ppm (d; 1H; J=2.5 Hz); 7.38 ppm (d; 1H; J=9 Hz).

C/ Preparation of 2-(2"-bromo-5$^1$-(2"-chloroethoxy)-phenyl)-2-methylpropylamine The preceding derivative (565 mg; 1.64 mmole) was dissolved in THF (10 ml) at room temperature. triphenylphosphine (645 mg; 2.46 mmole), chloroethanol (196 mg; 160 µl; 2 mmole) and finally DEAD (428 mg; 390 µl; 2.46 mmole) were added. The reaction mixture was refluxed for 2 h. The solvent was evaporated off under reduced pressure. The residue was purified by chromatography on a silica column (eluent: cyclohexane-ethyl acetate, 5/1). The N-2-(2'-bromo-5'-(2"-chloroethoxy)-phenyl)-2-methylpropyl—N-(tert-butyloxycarbonyl)-amine obtained in the form of a colorless oil (428 mg) was dissolved in dichloromethane (30 ml). Trifluoroacetic acid (3 ml) was added with stirring, and stirring was continued at room temperature for 1 h. The reaction mixture was washed with a saturated potassium bicarbonate solution (2×30 ml), dried and filtered. After evaporating off the solvent under reduced pressure, the desired product was obtained as a yellowish oil.
Yield: 64%
Physical characteristics:
 $^1$H NMR: (CDCl$_3$) 1.44 ppm (s; 6H); 1.73 ppm (sl; 2H); 3.22 ppm (sl; 2H); 3.79 ppm (t; 2H; J=6 Hz); 4.18 ppm (t; 2H; J=6 Hz); 6.60 ppm (dd; 1H; J=9–3 Hz); 6.89 ppm (d; 1H; J=3 Hz); 7.44 ppm (d; 1H; J=9 Hz). $^{13}$C NMR: (CDCl$_3$) 26.49 ppm; 42.09 ppm 50.34 ppm; 53.73 ppm; 68.45 ppm; 112.26 ppm; 113.77 ppm; 118.58 ppm; 136.99 ppm; 145.15 ppm; 157.93 ppm.

D/ Preparation of 6-(2'-chloroethoxy)-4,4'-dimethylbenzisoselenazine

This compound was obtained, using a procedure which was very similar to that for the derivative of Example 1/D from the preceding derivative, in the form of colorless crystals.
Yield: 48%
Physical characteristics:
 $^1$H NMR: (CDCl$_3$) 1.24 ppm (s; 6H); 3.22 ppm (sl; 3H); 3.77 ppm (t; 2H; J=6 Hz); 4.18 ppm (t; 2H; J=6 Hz); 6.66 ppm (dd; 1H; J=8–2.5 Hz); 6.91 ppm (d; 1H; J=8 Hz); 7.04 ppm (d; 1H; J=2.5 Hz).
 MS: (IE; 70 eV) 305 (M$^+$; 90%); 276 (100%); 213 (60%).

E/ Preparation of 4,4-dimethyl-6-(2'-(4"-methylpiperazine-1"-yl)ethoxy)-benzisoselenazine: BXT-51080

The preceding derivative (86 mg; 0.28 mmole) was dissolved in N-methylpiperazine (2.83 g; 3.15 ml; 28 mmole). This solution was heated for 22 h at a temperature of 60–70° C. After addition of dichloromethane (50 ml), the solution was washed with 25 ml of a saturated sodium bicarbonate solution then with 25 ml of a saturated sodium chloride solution, dried over sodium sulfate then filtered. The solvent was evaporated off under reduced pressure. The desired product was obtained as a yellow oil after purification by liquid chromatography on an alumina oxide column (eluent: cyclohexane-ethyl acetate, 1/1).
Yield: 71%
Physical characteristics:
 $^1$H NMR: (CDCl$_3$) 1.23 ppm (s; 6H); 2.27 ppm (s; 3H); 2.47 ppm (m; 4H); 2.60 ppm (m; 4H); 2.78 ppm (t; 2H; J=6 Hz); 3.20 ppm (sl; 2H); 3.34 ppm (sl; 1H); 4.04 ppm (t; 2H; J=6 Hz); 6.66 ppm (dd; 1H; J=9–2.5 Hz); 6.68 ppm (d; 1H;

J=9 Hz); 7.05 ppm (d; 1H; J=2.5 Hz). $^{13}$C NMR: (CDCl$_3$) 28.54 ppm; 33.36 ppm; 46.30 ppm; 53.85 ppm; 55.30 ppm; 57.51 ppm; 61.46 ppm; 66.25 ppm; 113.27 ppm; 115.27 ppm; 120.09 ppm; 125.96 ppm; 144.45 ppm; 157.46 ppm.

MS: (IE; 70 eV) 369 (M$^+$; 30%); 127 (70%); 113 (100%); 70 (50%).

II. EXAMPLES OF APPLICATIONS

The operating procedures described below are non limiting examples of applications of the method of the invention.

EXAMPLE 13

Measurement of the Glutathione Peroxidase Activity of Compounds with General Structure I To 1.5 ml of HEPES buffer, 50 mM, pH=7.3, containing 0.2 mM of DTPA, 0.144 mM of NADPH, 2.2 mM of reduced glutathione and 1.1 U/ml of glutathione disulfide reductase, pre-equilibrated for 2 minutes at 37° C., 100 µl of an ethanolic mother solution of the compound to be tested or 100 µl of absolute ethanol (blank) was added. Each compound was tested at a final concentration of 20 µM.

Subsequently, 50 µl of the following was added:

tertiobutyl hydroperoxide (t-BuOOH), 6.6 mM in ultrapure water;

or hydrogen peroxide (H$_2$O$_2$), 1.6 mM in ultrapure water;

or the hydroperoxide of linoleic acid (18:2-OOH) prepared using soya lipoxygenase (see M. O. Funk et al., Lipids, (1976), 11, pp 113–117), 3.3 mM in a water/ methanol mixture, 85/15 (V/V). The glutathione peroxidase activity was measured at 37° C. by measuring the reduction in absorbance at 340 nm over 5 minutes. The initial enzymatic rate or activity was proportional to the slope of the plot of absorbance against time.

The catalytic activity for oxygen reduction in the test compounds corresponded to the rate of consumption of NADPH in the absence of hydroperoxide. When this rate was significantly greater than that of the control, the corresponding glutathione oxidase activity could be verified directly by measuring the kinetics of dissolved oxygen consumption using a Clark electrode.

The results for the glutathione peroxidase activity obtained are shown in Table 1. They are expressed in nmoles of hydroperoxide reduced per minute.

These results show that compounds with general formula I described in the present invention catalyse the reduction of hydrogen peroxide or an organic hydroperoxide in the presence of glutathione GSH.

EXAMPLE 14

Measurment of Reducing Activity by Monoelectronic Transfer

The capacity of molecules with general structure I of the present invention to catalyse the reduction of an oxidizing entity by monoelectronic transfer in the presence of glutathione GSH, was demonstrated by spectrophotometric measurement of the reduction of ferric cytochrome c to ferrous cytochrome c, at pH=7.3 and at 37° C., as a function of time.

The reaction medium was constituted by a potassium phosphate buffer, 100 mM (pH=7.3) containing 75 µM of ferric cytochrome c, 250 µM of glutathione GSH, 0.1 mM of DTPA, 10 µg/ml of SOD and 110 U/ml of catalase. After addition of the compound to be tested, (10 µM in the reaction medium), the increase in absorbance at 550 nm was measured over 15 minutes.

The rate of formation of ferrous cytochrome c was proportional to the slope of the plot of absorbance against time (V, expressed in absorbance units per minute) and was compared with that observed in the presence of glutathione GSH, 250 µM and in the absence of the test compound (V$_{GSH}$), all other conditions being the same. The corresponding results are shown in Table 2.

These results demonstrate that compounds with general structure I described in the present invention catalyse the monoelectronic reduction of molecules in which the oxidizing power is thermodynamically greater than or equal to that of ferric cytochrome c, in the presence of excess glutathione GSH. Given that these compounds do not reduce oxygen in the presence of glutathione GSH, they behave as traps for oxidizing free radicals and chain reaction initiators without concomitant production of active forms of oxygen.

This constitutes one of the major advantages of organoselenium molecules with general structure I as opposed to the numerous other organoselenium molecules which reduce oxygen to a cytotoxic superoxide.

The antioxidizing compounds with general structure I showed no toxic effect on endothelial cells at a concentration of less than or equal to 15 µM.

EXAMPLE 15

Protection of Endothelial Cells Subjected to an Oxidizing Stress Induced by Linoleic Acid Hydroperoxide Human endothelial cells were cultivated at 37° C. in Leighton tubes and in an atmosphere of saturated humidity constituted by a gaseous mixture of 95% air and 5% of CO$_2$. The culture medium was constituted by an EGM (Clonetics) medium, pH=7.4 containing 2% of foetal calf serum, 10 ng/ml of recombinant human growth factor EGF, 10 µg/ml of heparin, 50 µm/ml of gentamicin and 50 µg/ml of amphotericin B.

When the cells were near confluence, they were incubated for one hour in the presence or absence (control) of the compound with general structure I to be tested, incorporated into the culture medium at a concentration of between 1 and 10 µM, all other conditions being the same. After washing the cells three successive times with a PBS buffer, they were incubated in the presence or absence (control) of linoleic acid hydroperoxide, 55 µM, in the culture medium. After one hour of incubation, the cells were washed three times with PBS buffer and stained using the May-Grunwald/Giemsa procedure which caused the nucleus to stain purple and the cytoplasm, light violet.

Microscopic examination of the slides obtained showed the adherent reference cells in which the morphology was characteristic of endothelial cells. The effect of linoleic acid hydroperoxide on these cells consisted firstly of a reduction of 25% to 35% in the cellular density and secondly in a drastic morphological change in about 70% of the remaining cells, whose nuclei were no longer distinguishable from the rest of the cellular body which had condensed and had a deep violet-black coloration. Separate exclusion experiments using trypan blue (a vital stain) indicated that more than 30% of the cells were dead. On the other hand, when the cells had been incubated with a compound with general formula I prior to treatment with the linoleic acid hydroperoxide, at least 80% of the endothelial cells were found to be morphologically normal.

These results demonstrate that compounds with general formula I described in the present invention are captured by the endothelial cells and the cells are protected against the deleterious effects of a fatty acid hydroperoxide.

EXAMPLE 16

Protection of Endothelial Cells Subjected to an Oxidizing Stress Induced by Hydrogen Peroxide Human endothelial cells were cultivated at 37° C. in 6-hole plates or Petri dishes (35 mm diameter) in an atmosphere of saturated humidity constituted by a gaseous mixture of 95% air and 5% of $CO_2$. The culture medium was constituted by a M 199 medium, pH=7.4, containing 20% of foetal calf serum, 2 mM of L-glutamine, 100 U/ml of penicillin and 100 µg/ml of streptomycin.

When the cells were confluent, they were incubated in the presence or absence (control) of a compound with general structure I in culture medium at a concentration of between 1 and 10 µM, all other conditions being the same. After washing the cells three successive times with a PBS buffer, they were incubated in the presence or absence (control) of hydrogen peroxide, 500 or 100 µM, in the reaction medium. The cells were then washed three times with PBS buffer. They were then stained using the May-Grunwald/Giemsa procedure which caused the nucleus to stain purple and the cytoplasm, light violet, or they were used to measure their ability to produce nitric oxide NO. (EDRF). The production of NO. by endothelial cells was made using a NO. electrode, after stimulation with bradykinin, 100 nM, using the procedure described by H. Tsukahara et al., (Biochem. and Biophys. Res. Comm., (1993), 193, pp 722–729).

Microscopic examination of the plates obtained after staining showed adherent reference cells in which the morphology was characteristic of endothelial cells. The effect of 500 µM hydrogen peroxide consisted essentially of a reduction in the cellular density of 70% to 80%. On the other hand, when the cells had first been treated with a compound with general formula I as described above in Example 7, more than 50% of the cellular density was preserved. As an example, about 70% of the cellular density was preserved when the cells had been previously incubated with compound BXT-51056.

Treatment with 100 µM hydrogen peroxide had no significant effect on cellular density. The cells appeared to be morphologically normal under the microscope. This treatment, however, resulted in a change in the NO. production of more than 90%. On the other hand, pretreatment of the endothelial cells with a compound with general formula I as described above, at a concentration of between 0.2 and 1 µM, resulted in a significant recovery of the normal response to bradykinin. As an example, pretreatment of the cells with compound BXT-51056 at a concentration of 1 µM led to a recovery of more than 80% of the normal response to bradykinin.

These results demonstrate that compounds with general formula I described in the present invention are captured by endothelial cells which they then protect against the deleterious effects of hydrogen peroxide.

EXAMPLE 17

Protection of Endothelial Cells Subjected to an Oxidizing Stress Induced by Polymorphonuclear Neutrophiles in the Presence of TNF-α

Human endothelial cells were cultivated at 37° C. in 25 cm³ flasks in an atmosphere of saturated humidity constituted by a gaseous mixture of 95% air and 5% of $CO_2$. The culture medium was constituted by an EGM (Clonetics) medium, pH=7.4, containing 2% of foetal calf serum, 10 ng/ml of recombinant human growth factor EGF, 10 µg/ml of heparin, 50 µm/ml of gentamicin and 50 µg/ml of amphotericin B.

When the cells were near confluence, they were incubated for one hour in the presence or absence (control) of the compound with general structure I to be tested, incorporated into culture medium at a concentration of between 1 and 10 µM, all other conditions being the same. After washing the cells three successive times with a PBS buffer, they were incubated in the presence or absence (control) of TNF-α (100 U/ml in the culture medium) and polymorpholonuclear neutrophiles (PMN), in a ratio of about 10 PMN per endothelial cell, prepared from heparinated human blood (see A. Boyum, Scand. J. Clin. Lab. Invest., (1968), 21, pp 77–89). After four hours of incubation, the cells were washed three times with PBS buffer and stained using the May-Grunwald/ Giemsa procedure which caused the nucleus to stain purple and the cytoplasm, light violet.

Microscopic examination of the stained flasks obtained showed the adherent reference cells in which the morphology was characteristic of endothelial cells. The effect of the PMNs on the cells, in the presence of TNF-α, consisted of a reduction of 30% to 40% in the endothelial cell density and a drastic change in more than 70% of the remaining adhered cells, whose nuclei were no longer distinguishable from the rest of the cellular body which had condensed and had a deep violet-black coloration. In this case, a large number of PMNs was observed adhered to the support, in particular against the external surface of the plasma membrane of the endothelial cells. On the other hand, when, prior to incubation of the endothelial cells with the PMNs and TNF-α, the cells were incubated in the presence of a compound with general formula I, the majority of the endothelial cells were found to be morphologically normal and free of adhering PMNs.

These results demonstrate that compounds with general formula I described in the present invention are captured by endothelial cells which are then protected against the deleterious effects of activated polymorphonuclear neutrophiles.

EXAMPLE 18

Viability Test on Endothelial Cells Subjected to an Oxidizing Stress Induced by Linoleic Acid Hydroperoxide Human endothelial cells were cultivated at 37° C. in multi-hole plates or Petri dishes in an atmosphere of saturated humidity constituted by a gaseous mixture of 95% air and 5% of $CO_2$. The culture medium was constituted by a M 199 medium, pH=7.4, containing 20% of foetal calf serum, 2 mM of L-glutamine, 100 U/ml of penicillin, 100 µg/ml of streptomycin and 1% by volume of a medium supplement containing heparin and a cell growth factor.

When the cells were near confluence, they were incubated for one hour in the presence or absence of one of the following compounds: BXT-51056, BXT-51072, BXT-51077, or ebelsen. Each of these compounds was incorporated at 4 µM into culture medium containing 2% of foetal calf serum, all other conditions being the same.

After washing the cells three successive times with a PBS buffer, they were incubated in the presence or absence (control) of linoleic acid hydroperoxide (18:2-OOH), 50 µM, in the culture medium defined above. After two hours incubation, the cells were washed three successive times with a PBS buffer, and they were incubated again in the 20% foetal calf serum defined initially. After about twenty hours, the viability of the cells was determined by measurement using the bromide of 3-(4,5-dimethylthiazol-2-yl)-2,5-diphenyl-2H-tetrazolium (MTT).

The results are shown in FIG. 1, expressed as the survival percentage with respect to the control and where the reference is shown by the black rectangle. It can be seen that of the compounds tested, only BXT-51056, BXT-51072 and BXT-51077 significantly protected the cells from death induced by 18:2-OOH.

As in Example 15, these results show that compounds with general formula I described in the present invention are captured by the endothelial cells which they then protect against the deleterious effects of a fatty acid hydroperoxide.

EXAMPLE 19

Protective Effect of Compounds BXT-51056, BXT-51072 and BXT-51077; Biochemical Quantification of Endothelial Changes Induced by Polymorphonuclear Neutrophiles in the Presence of TNF-α

Human endothelial cells were cultivated under the same conditions as those described for Example 18.

When the cells were near confluence, they were incubated for one hour in the presence or absence of the following compounds: BXT-51072, BXT-51077 or pentoxifylline. Compounds BXT-51072 and BXT-51077, each at 10 μM, and the pentoxifylline, at 50 μM, were incorporated in culture medium containing 2% of foetal calf serum, all other conditions being the same. The cells were then washed with a PBS buffer, The cells which had not been pretreated with the test compounds were then incubated or not (control) in the presence of TNF-α, at 1 ng/ml, and/or polymorphonuclear neutrophiles (PMN), as indicated in Example 15, in culture medium containing 2% of foetal calf serum. The pretreated cells were incubated under the same conditions, but the culture medium also contained the test compound at the concentration defined above. After firstly one hour of incubation and then after three and a half hours of incubation, the culture medium was collected, the cellular mass was washed three times with a PBS buffer and the adhered PMNs were lysed. Myeloperoxidase (MPO), an enzyme specifically contained in PMNs, was then measured in the cell lysates obtained to evaluate adhesion of the PMNs on the endothelial cells. The von Willebrandt factor (vWf) liberated in the culture medium by the endothelial cells was measured after three and a half hours of incubation, as a label of the changes in the cells.

Incubation of the endothelial cells in the presence of PMN and TNF-α led to a very significant increase in the quantity of MPO and vWf with respect to the respective controls (PMN alone, and endothelial cells alone respectively), meaning the adhesion of activated PMNs to the endothelial cells and changes in the latter.

Figure 2:
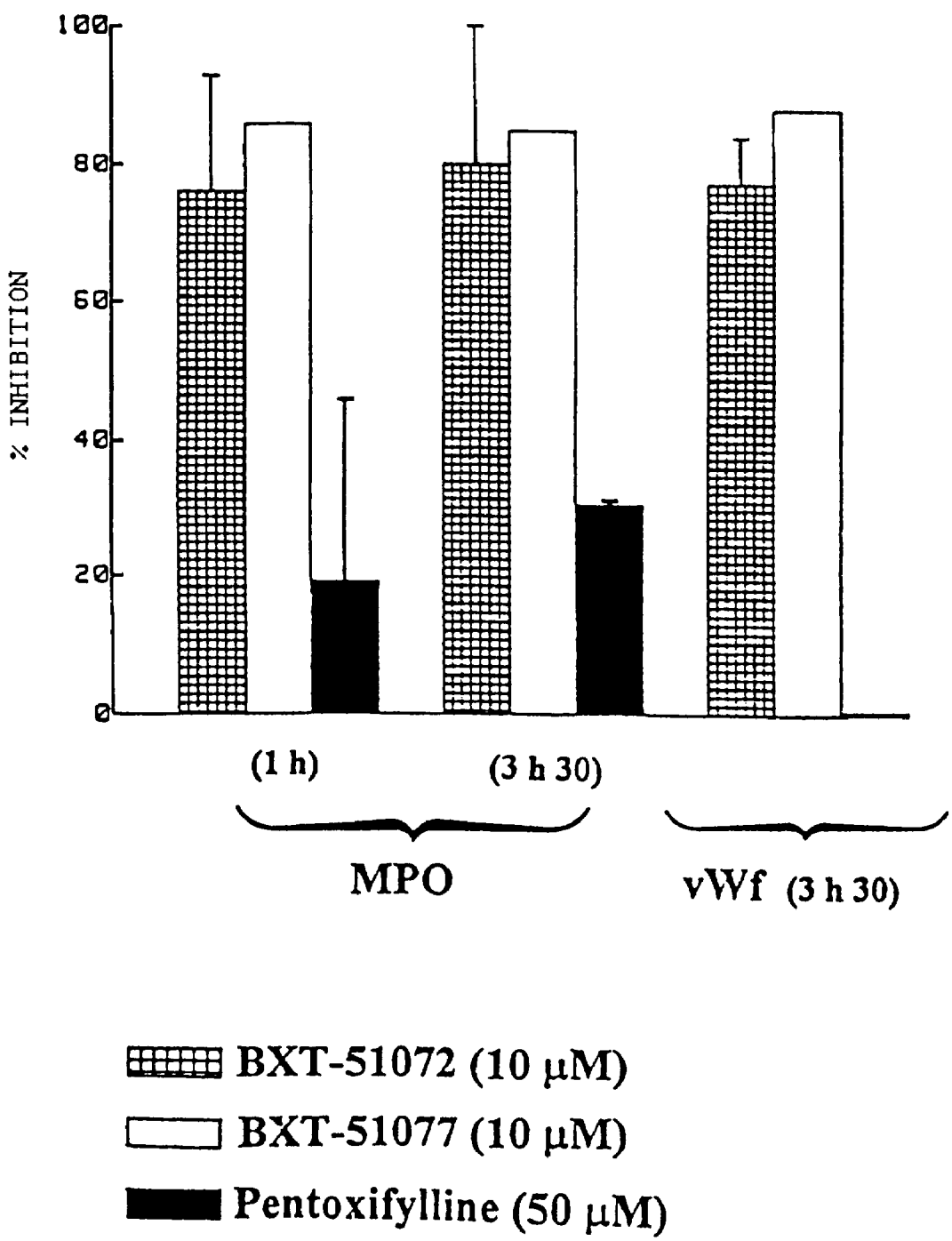
FIG. 2 also shows a histogram obtained from a study of the protective effect of compounds BXT-51056, BXT-51072 and BXT-51077 of the invention against endothelial changes induced by polymorphonuclear neutrophiles in the presence of TNF-α, as described in Example 19.

The results obtained for the three compounds tested are shown in FIG. 2. They are expressed as the percentage inhibition by referring the MPO and vWf measurements to the respective concentrations of MPO and vWf determined when the endothelial cells were incubated with TNF-α and PMNs.

These results show that compounds BXT-51072 and BXT-51077 inhibit the adhesion of PMN induced by TNF-α, much more effectively than pentoxifylline. In contrast to pentoxifylline, they also protect endothelial cells against the deleterious effects of activated PMNS.

EXAMPLE 20

Protective Effect of Compounds BXT-51072 and BXT-51077; Biochemical Quantification of the Endothelial Production of Interleukin 8 Induced by TNF-α

Human endothelial cells were cultivated under the same conditions as those described for Example 18.

When the cells were near confluence, they were incubated for one hour in the presence or absence of the following compounds: BXT-51072, BXT-51077 or ebselen. Each of these compounds was incorporated into culture medium containing 2% of foetal calf serum at 10 μM, all other conditions being the same. After elimination of the culture medium, the cells were incubated in the presence or absence (control) of TNF-α, at 0.1, 1 or 10 ng/ml in the same culture medium as before, which contained or did not contain the test compound at 10 μM. After four hours of incubation, the interleukin 8 (IL-8) in the culture medium was measured.

Figure 3:
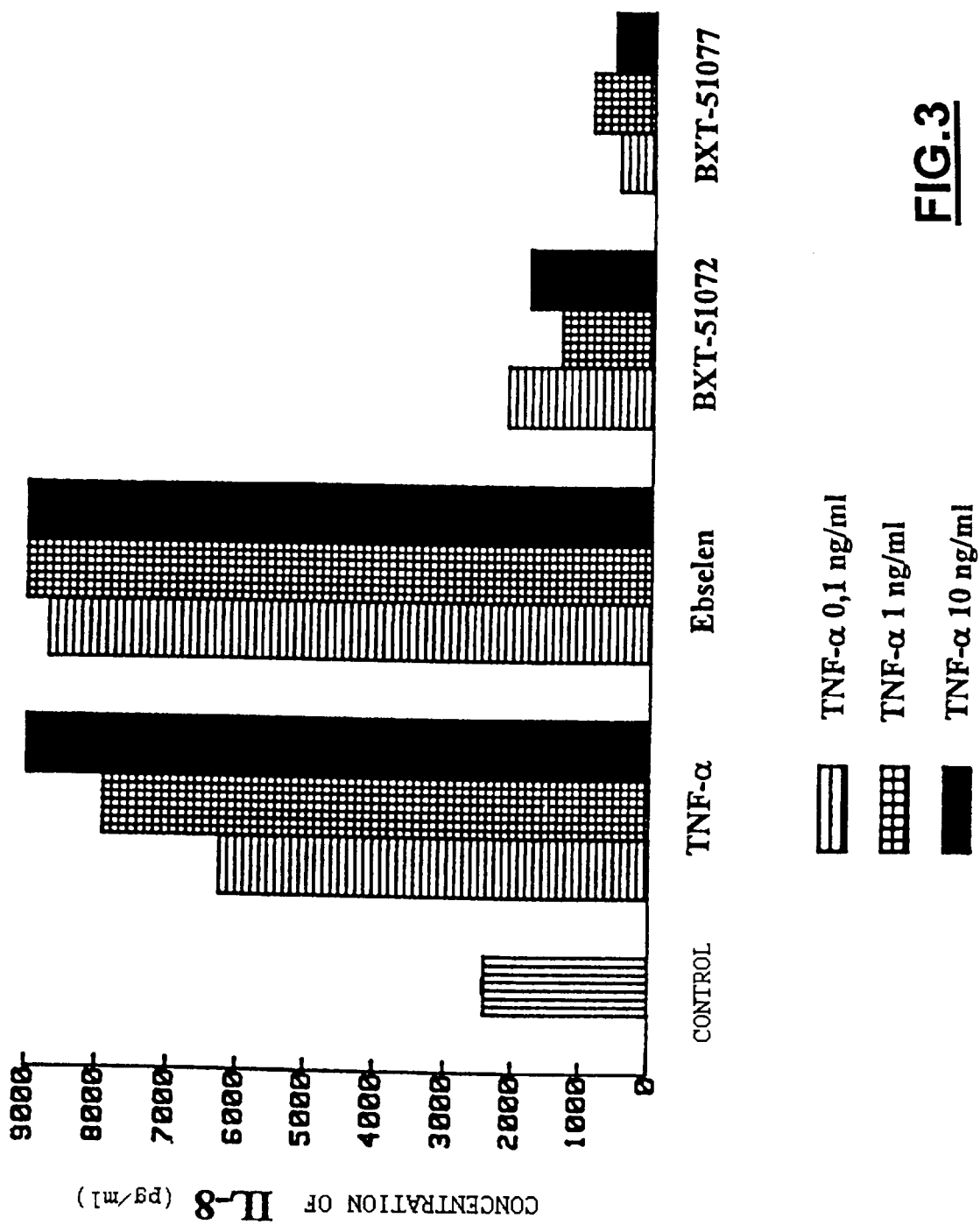
FIG. 3 shows a histogram similar to that of FIG. 2 in a study of the protective effect of compounds BXT-51072 and BXT-51077 of the invention on the production of endothelial interleukin 8 induced by TNF-α as described in Example 20.

The results obtained are shown in FIG. 3. These results show that incubation of cells in the presence of TNF-α increased the production of IL-8 in the culture medium, and that treatment of cells with compounds BXT-51072 and BXT-51077 inhibit this effect by at least 70%, while ebselen had no inhibiting effect.

These results show that these compounds can act against antagonists of TNF-α in terms of liberation of interleukin 8 by endothelial cells.

EXAMPLE 21

Protection of Endothelial Cells Againts the Toxicity of Interleukin 1

Human endothelial cells were cultivated under the same conditions as those described for Example 18.

When the cells were near confluence, they were incubated for one hour in the presence or absence of the following compounds: BXT-51072, BXT-51077, each of these compounds being at 10 μM in culture medium containing 2% of foetal calf serum, all other conditions being the same. The cells were then washed three times with a PBS buffer. The cells which had not been pretreated by a compound were incubated in the presence or absence (control) of interleukin 1α (IL-1α), at 50 U/ml, in the same culture medium. The cells which had been pretreated were incubated under the same conditions, but the medium contained or did not contain the test compound at the concentration indicated above. After four hours of incubation, the von Willebrandt factor (vWf) in the culture medium was measured.

Figure 4:
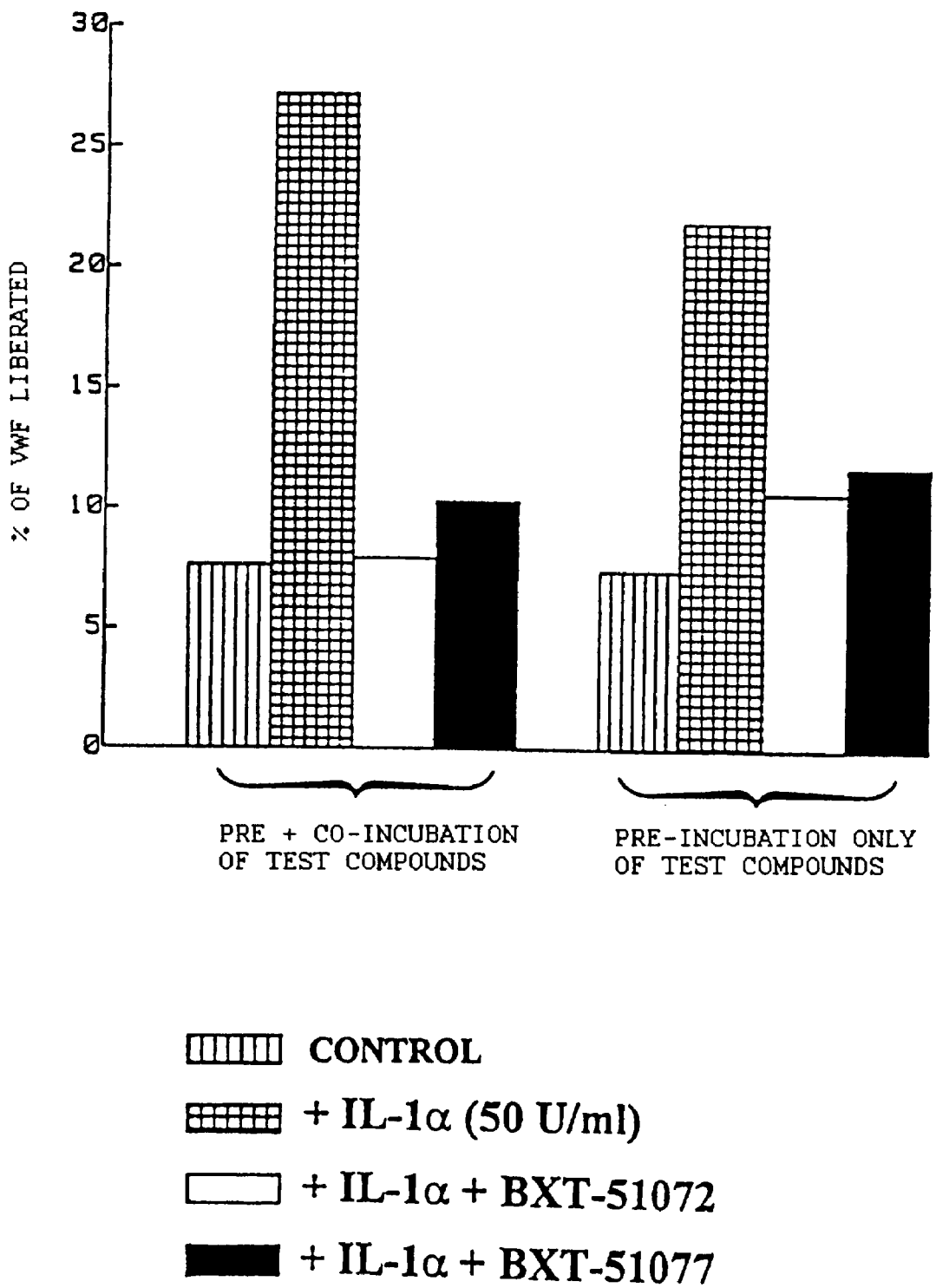
FIG. 4 shows a histogram similar to those of FIGS. 2 and 3 with compounds BXT-51072 and BXT-51077 of the invention in a study of the protection of endothelial cells against the toxicity of interleukin 1, as described in Example 21.

The results obtained are shown in FIG. 4. These results show that the increase in the liberation of vWf induced by IL-1 is inhibited by more than 70% by treating the cells with compound BXT-51072 or BXT-51077, whether or not each is present during incubation of the cells with interleukin 1.

These results show that these compounds are captured by endothelial cells and can act as antagonists of interleukin 1 as regards liberation of von Willebrandt factor by endothelial cells.

EXAMPLE 22

Inhibition of Endothelial Expression of P-Selection Induced by TNF-α

Human endothelial cells were cultivated under the same conditions as those described for Example 18.

When the cells were near confluence, they were incubated for one hour in the presence or absence of BXT-51072 at 10 μM in culture medium containing 2% of foetal calf serum, all other conditions being the same. The cells were then washed three times with a PBS buffer. The cells which had not been pretreated by a compound were incubated in the presence or absence (control) of TNF-α, at 1 ng/ml, in the same culture medium. The pretreated cells were incubated under the same conditions, but the medium also contained BXT-51072 at 10 μM. After 3 to 4 hours of incubation, the cells were washed with a PBS buffer and fixed with 2% formaldehyde in a PBS buffer. Expression of P-selectin from the cells was then measured by an ELISA determination by successively incubating the cells in the presence of a monoclonal anti-P-selectin mouse antibody and a mouse anti-antibody labelled with alkaline phosphatase, revealing by addition of paranitrophenyl phosphate, the hydrolysis of which was followed at 405 nm. The results obtained show that incubation of cells in the presence of TNF-α induced an increase in the expression of P-selectin by a factor of 4, which was inhibited by more than 90% when the cells were treated with compound BXT-51072.

These results demonstrate that these compounds can inhibit the expression of a cellular adhesion molecule such as P-selectin, induced by TNF-α.

EXAMPLE 23

Absence of Toxicity of Compounds BXT-51056 and BXT-51072 in a Culture of Endothelial Cells in Vitro Human endothelial cells were cultivated under the same conditions as those described for Example 18, in 96-hole plates.

When the cells were near confluence, they were incubated or not (control) for 24 or 48 hours in the presence of BXT-51056 or BXT-51072 incorporated into the culture medium at a concentration of no more than 10 $\mu$M. After 24 or 48 hours, the cells were rinsed three times with a PBS buffer and the viability of the cells was measured using the bromide of 3-(4,5-dimethylthiazol-2-yl)-2,5-diphenyl-2H-tetrazolium (MTT).

No significant difference from the reference was measured, demonstrating that compounds BXT-51056 and BXT-51072 were not toxic to endothelial cells at a concentration of no more than 10 $\mu$M.

EXAMPLE 24

Tolerance of Compound BXT-51072 after Repeated Oral Administration to the Rat in Vivo Male adult Sprague-Dawley rats were randomly divided into 4 groups. To one group of 10 rats and another group of 15 rats, one dose of 10 $\mu$moles and one dose of 100 $\mu$moles per kilogram of body weight of BXT-51072 were respectively orally administered (force feeding) each day for 14 days. These doses were administered using an aqueous solution containing 1% of sodium carboxymethylcellulose (CMC). using the same procedure, a third group of 12 rats received only the vector (1% CMC) and a third group of 3 rats received no force feeding.

In order to evaluate any toxicity in the test compound, all the animals were regularly weighed over the 14 days. Their appearance and behavior were observed daily.

Figure 6:
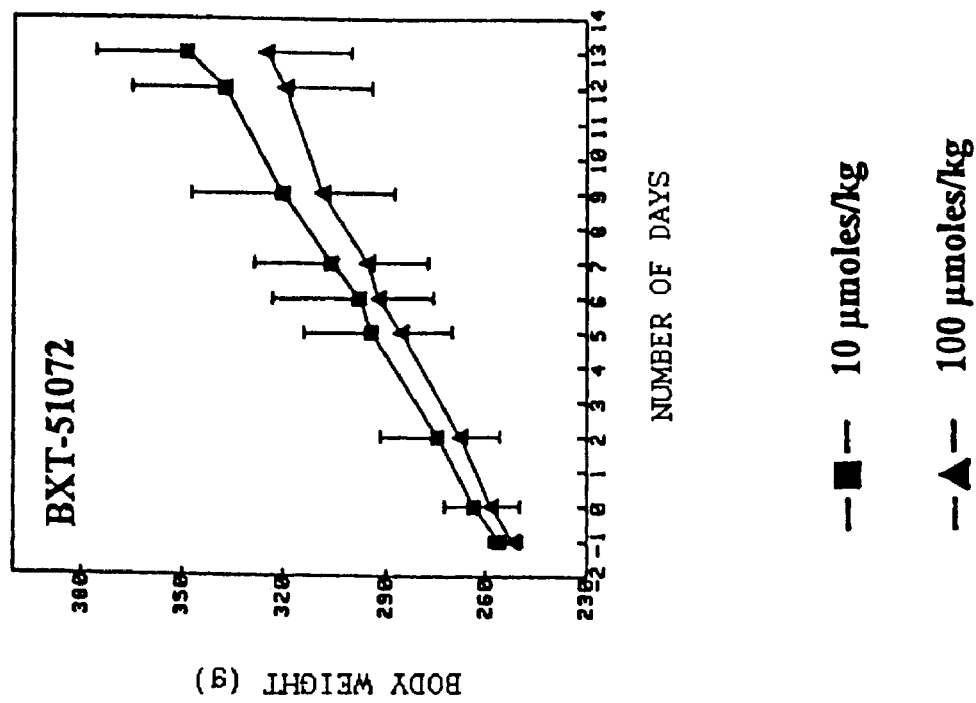
FIGS. 5 and 6 show the tolerance results obtained respectively with the control (FIG. 5) and compound BXT-51072 of the invention (FIG. 6) after repeated oral administration to the rat in vivo under the test conditions of Example 24.
Figure 5:
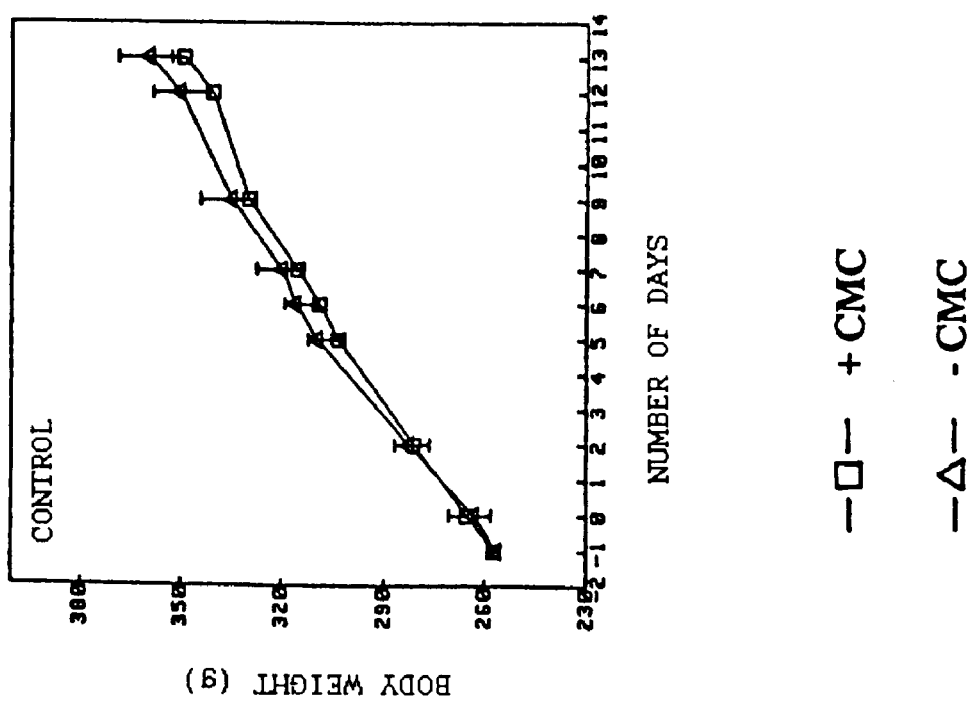

After 14 days of treatment, none of the animals had died. About 16 hours after the final administration, the rats were anaesthetised with ketamine and blood samples were taken by intra-cardiac tapping to measure different hematological and biochemical parameters. The weight curves of the animals are shown in FIGS. 5 and 6 and Table 3 summarises the results of measurements carried out on the blood of the animals and the corresponding deviations.

Despite a slight slowing in weight gain at the higher dose of BXT-51072 of the invention (100 $\mu$moles/kg, FIG. 6), there was no other sign of toxicity (Table 3). These results show that compound BXT-51072 of the invention was tolerated well by the rat in vivo after repeated oral administration.

TABLE 1

| | Glutathione peroxidase activity (nmoles of hydroperoxide reduced/min) pH = 7.3; 37° C.; [GSH] = 2 mM | | |
|---|---|---|---|
| | t-BuOOH | $H_2O_2$ | 18:2-OOH |
| BXT-51056 (Ex. 1) | 8.8 | 12 | 29.9 |
| BXT-51058 (Ex. 3) | 3.1 | 2.1 | 22.9 |
| BXT-51059 (Ex. 4) | 0.2 | 0.1 | 0.8 |
| BXT-51072 (Ex. 8) | 27.4 | 42.0 | — |
| BXT-51075 (Ex. 6) | 3.2 | 5.9 | — |
| BXT-51076 (Ex. 7) | 4.5 | 6.6 | — |
| BXT-51077 (Ex. 11) | 35.4 | — | — |
| BXT-51078 (Ex. 10) | 16.5 | — | — |

TABLE 2

| | $V/V_{GSH}$ |
|---|---|
| BXT-51056 (Ex. 1) | 4.8 |
| BXT-51057 (Ex. 2) | 1.5 |
| BXT-51059 (Ex. 4) | 2.9 |

TABLE 3

| | | HEMATOLOGY | | | | | | | | | | |
|---|---|---|---|---|---|---|---|---|---|---|---|---|
| | n | GR [T/l] | HB [mM] | HCT | VGM [fl] | GB [G/l] | NEU [%] | EOS [%] | BAS [%] | LYM [%] | MON [%] | PLT [G/l] |
| CONTROL | | | | | | | | | | | | |
| (−CMC) | 3 | 6.79 (0.16) | 9.11 (0.25) | 0.41 (0.01) | 60.5 (1.39) | 8.83 (2.05) | 12 (2) | 0 | 0 | 88 (2) | 0 | 654 (146) |
| (+CMC) | 6 | 6.76 (0.29) | 8.90 (0.20) | 0.40 (0.01) | 60.0 (2.36) | 8.83 (2.16) | 12 (3) | 0 | 0 | 87 (3) | 1 (0.4) | 682 (197) |
| BXT-51072 | | | | | | | | | | | | |
| 10 ($\mu$moles/kg) | 4 | 6.88 (0.36) | 9.08 (0.31) | 0.41 (0.01) | 59.8 (2.36) | 8.45 (1.99) | 18 (5) | 0 | 0 | 82 (5) | 0 | 541 (280) |

TABLE 3-continued

| | | | | | | | | | | | | |
|---|---|---|---|---|---|---|---|---|---|---|---|---|
| 100 (μmoles/kg) | 7 | 7.44 (0.40) | 9.46 (0.46) | 0.43 (0.02) | 57.6 (1.99) | 7.57 (1.83) | 18 (7) | 1 (0.8) | 0 | 81 (8) | 0 | 517 (200) |

| | | BIOCHEMISTRY | | | | | | | |
|---|---|---|---|---|---|---|---|---|---|
| | n | $Na^+$ [mM] | $K^+$ [mM] | $Cl^-$ [mM] | Urea [mM] | Prot [g/l] | PAL [UI/l] | ALAT [UI/l] | ASAT [UI/l] |
| CONTROL | | | | | | | | | |
| (−CMC) | 3 | 143 (0) n = 2 | 4.7 (0.2) n = 2 | 94 (0.6) | 3.65 (0.29) | 55.1 (2.5) | 314 (91) | 63 (12) | 145 (15) |
| (+CMC) | 6 | 144 (0.6) n = 3 | 4.7 (0.5) n = 3 | 95 (0.8) | 4.73 (0.83) | 54.8 (2.1) | 334 (70) | 58 (6) | 124 (29) |
| BXT-51072 | | | | | | | | | |
| 10 (μmoles/kg) | 4 | 143 n = 1 | 5.0 n = 1 | 93 (1.4) n = 2 | 4.03 (0.68) | 53.9 (0.4) n = 2 | 320 (84) | 50 (9) n = 3 | 136 (60) n = 3 |
| 100 (μmoles/kg) | 7 | 143 (0) n = 2 | 5.0 (0.1) n = 2 | 93 (1.3) n = 4 | 4.05 (0.43) n = 5 | 55.0 (2.6) n = 4 | 310 (66) n = 5 | 58 (12) n = 4 | 133 (18) n = 4 |

Abbreviations: GR, Red cells; HB, Hemoglobin; HCT, Hematocrit; VGM, Average cell volume of GR; GB, White cells; NEU, neutrophiles; EOS, eosinophiles; BAS, basophiles; LYM, Lymphocytes; MON, Monocytes; PLT, Platelets; Prot, Proteins; PAL, Alkaline phosphalase; ALAT, Alanine aminotransferase; ASAT, Aspartale aminotransferase.

Scheme 1

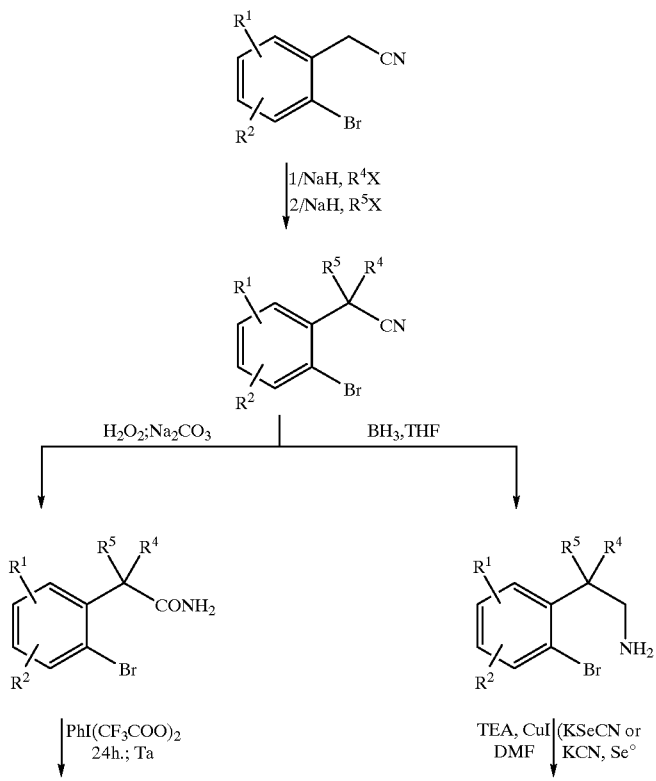

-continued

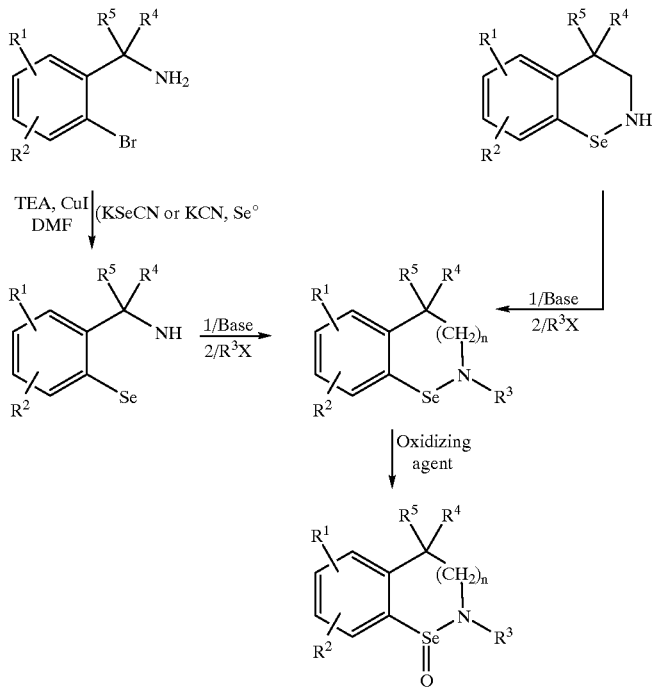

We claim:
1. A method for storing a biological organ transplant graft for transplanting by placing said biological organ graft in an adapted storage medium comprising the step of adding to said storage medium at least one compound of formula (I):

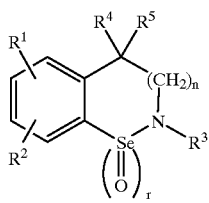

wherein:
R$^1$ is selected from the group consisting of hydrogen; lower alkyl; —OR$^6$; —(CH$_2$)$_m$NR$^6$R$^7$; —(CH$_2$)$_q$NH$_2$; —(CH$_2$)$_m$NHSO$_2$(CH$_2$)$_2$NH$_2$; —CN; —SO$_3$H; F; Cl; Br; I; —(CH$_2$)$_m$R$^8$; —(CH$_2$)$_m$COR$^8$; —S(O)NR$^6$R$^7$; SO$_2$NR$^6$R$^7$; —CO(CH$_2$)$_p$COR$^8$; and R$^9$;
R$^2$ is selected from the group consisting of hydrogen; lower alkyl; —OR$^6$; —(CH$_2$)$_m$NR$^6$R$^7$); —(CH$_2$)$_q$NH$_2$; —(CH$_2$)$_m$NHSO$_2$(CH$_2$)$_2$NH$_2$; —CN; —SO$_3$H; F; Cl; Br; I; —(CH$_2$)$_m$R$^8$; —(CH$_2$)$_m$COR$^8$; —S(O)NR$^6$R$^7$; —SO$_2$NR$^6$R$^7$; —CO(CH$_2$)$_p$COR$^8$ and R$^9$;
R$^3$ is selected from the group consisting of hydrogen; lower alkyl; aralkyl; substituted aralkyl; —(CH$_2$)$_m$COR$^8$; —(CH$_2$)$_q$R$^8$; —CO(CH$_2$)$_p$COR$^8$; —(CH$_2$)$_m$SO$_2$R$^8$; and —(CH$_2$)$_m$S(O)R$^8$;
R$^4$ is selected from the group consisting of lower alkyl; aralkyl; substituted aralkyl; —(CH$_2$)$_p$COR$^8$; and —(CH$_2$)$_p$R$^8$; and F;
R$^5$ is selected from the group consisting of lower alkyl; aralkyl; and substituted aralkyl;
R$^6$ is selected from the group consisting of lower alkyl; aralkyl; substituted aralkyl; —(CH$_2$)$_m$COR$^8$; and (CH$_2$)$_q$R$^8$;

R$^7$ is selected from the group consisting of lower alkyl; aralkyl; substituted aralkyl; and —(CH$_2$)$_m$COR$^8$;
R$^8$ is selected from the group consisting of lower alkyl; aralkyl; substituted aralkyl; aryl; substituted aryl; heteroaryl; substituted heteroaryl; hydroxy; lower alkoxy; and R$^9$;
R$^9$ is selected from the group consisting of:

R$^9$ =

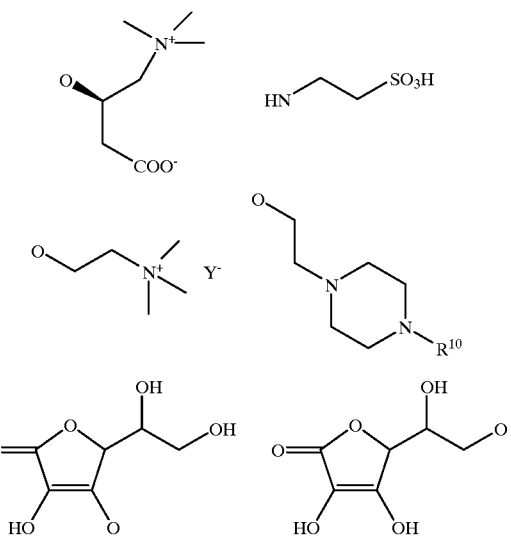

R$^{10}$ is selected from the group consisting of hydrogen; lower alkyl; aralkyl; substituted aralkyl; aryl and substituted aryl;
y$^-$ represents the anion of a pharmaceutically acceptable acid:
n=0 or 1;
m=0, 1 or 2;

p=1, 2 or 3;
q=2, 3 or 4;
r=0 or 1;
and pharmaceutically acceptable salts thereof of acids or bases;
there being no more than one substituent $R^9$ in each molecule of formula I.

2. The method of claim 1, wherein said organ transplant graft is selected from the group consisting of heart, liver, kidney and lung.

3. A method for storing a biological organ transplant graft for transplanting by placing said biological organ graft in an adapted storage medium comprising the step of adding to said storage medium 4,4-dimethyl-benzisoselenazine or a pharmaceutically acceptable acid or base salt thereof.

4. The method of claim 3, wherein said organ transplant graft is selected form the group consisting of heart, liver, kidney and lung.

5. The method of claim 1, wherein the compound of formula I is added to the storage medium at a concentration ranging from 0.1% to 5% by weight of the storage medium.

6. The method of claim 1, wherein the compound of formula I is added to the storage medium at a concentration ranging from 0.1% to 1% by weight of the storage medium.

7. The method of claim 3, wherein the said 4,4-dimethyl-benzisoselen-azine or pharmaceutically acceptable acid or base salt thereof is added to the storage medium at a concentration ranging from 0.1% to 5% by weight of the storage medium.

8. The method of claim 3, wherein the said 4,4-dimethyl-benzisoselenazine or pharmaceutically acceptable acid or base salt thereof is added to the storage medium at a concentration ranging form 0.1% to 1% by weight of the storage medium.

9. A method for storing a biological organ transplant graft for transplanting by placing said biological organ graft in an adapted storage medium comprising the step of adding to said storage medium a benzisoselen-azoline or -azine compound selected from the group consisted of 3,3-N dimethyl-benzisoselenazoline, 2-acetyl-3,3-dimethyl-benzisoselenazoline, 3,3-dimethyl-2-ethyl-benzisoselenazoline, 3-3-dimethyl-benzisoselenazoline-1-oxide, 3,3-dimethyl-7-nitro-benzisoselenazoline, 3,3'-dimethyl-5-nitro-benzisoselenazoline, 3,3-dimethyl-7-fluoro-benzisoselenazoline, 4-4-dimethyl-benzisoselenazine-1-oxide, 4,4-dimethyl-2-ethyl-benzisoselenazine, 4,4-dimethyl-6-methoxy-benzisoselenazine, 4,4-dimethyl-6-(2'-(1"-methylpiperazine 1"-yl)ethoxybenzisoselenazine and pharmaceutically acceptable acid or base salts thereof.

10. The method of claim 9, wherein said organ transplant graft is selected from the group consisting of heart, liver, kidney and lung.

11. The method of claim 10, wherein the benzisoselenazoline or -azine derivative is added to the storage medium at a concentration ranging from 0.1% to 5% by weight of the storage medium.

12. The method of claim 11, wherein the benzisoselenazoline or -azine derivative is added to the storage medium at a concentration ranging from 0.1% to 1% by weight of the storage medium.

* * * * *

UNITED STATES PATENT AND TRADEMARK OFFICE
CERTIFICATE OF CORRECTION

PATENT NO. : 6,093,532
DATED : July 25, 2000
INVENTOR(S) : IRENE ERDELMEIER et al It is certified that error appears in the above-indentified patent and that said Letters Patent is hereby corrected as shown below:

On the Title Page

Under "[30] Foreign Application Priority Data",

Change "July 4, 1994" to --April 7, 1994--

Signed and Sealed this

Twenty-fourth Day of April, 2001

Attest:

NICHOLAS P. GODICI

Attesting Officer     Acting Director of the United States Patent and Trademark Office